United States Patent [19]

Hinshaw et al.

[11] 4,199,355

[45] Apr. 22, 1980

[54] POSITIVE-WORKING IMMOBILE PHOTOGRAPHIC COMPOUNDS AND PHOTOGRAPHIC ELEMENTS CONTAINING SAME

[75] Inventors: Jerald C. Hinshaw, Penfield; Paul B. Condit, Pittsford, both of N.Y.

[73] Assignee: Eastman Kodak Company, Rochester, N.Y.

[21] Appl. No.: 589,977

[22] Filed: Jun. 24, 1975

[51] Int. Cl.$^2$ .................... G03C 5/54; G03C 1/40; G03C 1/76; G03C 1/10

[52] U.S. Cl. ............................ 430/226; 430/959; 430/566; 430/542; 430/599; 430/362; 430/955; 430/202; 430/212; 430/219; 430/234; 430/242; 430/544; 430/566; 430/607; 430/621

[58] Field of Search .................. 96/3, 29 D, 77, 76 R, 96/66.3, 95, 99, 100, 73, 74, 111, 109, 107, 101, 96, 119 R; 260/192, 197, 205, 307 A, 455 R, 343.2, 468 R, 468 E, 468 K, 469, 308 R, 308 C, DIG. 26

[56] References Cited

U.S. PATENT DOCUMENTS

| | | | |
|---|---|---|---|
| 2,846,307 | 8/1958 | Woolley | 96/55 |
| 3,241,963 | 3/1966 | Green et al. | 96/3 |
| 3,245,790 | 4/1966 | Downey et al. | 96/3 |
| 3,347,672 | 10/1967 | Downey et al. | 96/3 |
| 3,443,939 | 5/1959 | Bloom et al. | 96/3 |
| 3,590,692 | 7/1971 | Bloom | 96/26 |
| 3,674,478 | 7/1972 | Grasshoff | 96/3 |
| 3,698,897 | 10/1972 | Gompf et al. | 96/3 |
| 3,728,113 | 4/1973 | Becker et al. | 96/3 |
| 3,854,945 | 12/1974 | Bush et al. | 96/3 |
| 3,880,658 | 4/1975 | Lestina et al. | 96/3 |

FOREIGN PATENT DOCUMENTS 1157506   7/1969   United Kingdom .

*Primary Examiner*—Richard L. Schilling
*Attorney, Agent, or Firm*—Joshua G. Levitt

[57] ABSTRACT

Photographic elements, processes for forming images in photographic elements and new compounds are disclosed. Generally, the invention relates to improved immobile compounds which can be used to provide positive images from negative recording-developing photographic materials such as negative silver halide emulsions. The compounds contain a photographically useful group such as a dye or dye precursor and are capable of releasing said photographically useful group under alkaline conditions, and are also capable of reaction with an oxidized silver halide developing agent before substantial release of said photographically useful group occurs, to provide a reaction product having a substantially lower rate of release of said photographically useful group.

47 Claims, No Drawings

POSITIVE-WORKING IMMOBILE PHOTOGRAPHIC COMPOUNDS AND PHOTOGRAPHIC ELEMENTS CONTAINING SAME

This invention relates to new compounds, photographic elements and processes of forming image records in photographic elements. In one aspect, this invention relates to image dye-providing materials which are immobile or ballasted compounds as incorporated into photographic elements. In another aspect, this invention relates to dye image-providing materials which can be used in image-transfer film units.

It is known in the art to use image dye-providing materials in photographic elements such as image-transfer film units. Image dye-providing materials which are initially mobile in the film units have been employed, for example, such as the mobile couplers and developers disclosed in Land, U.S. Pat. No. 2,698,244 issued Dec. 28, 1954, where a dye is synthesized in the receiver layer. Performed mobile dyes which reacted with mobile oxidized color developers are disclosed in U.S. Pat. No. 2,774,668. Further disclosures of the use of mobile performed dyes are found in Rogers, U.S. Pat. No. 2,983,606 issued May 8, 1961. However, the initially mobile dye image-providing materials have certain disadvantages in photographic elements: they can diffuse prematurely to adjacent layers affecting interimage color reproduction and they remain reactive when diffusing through adjacent layers after development where they can react to cause drop-off in color scales, and the like.

Image dye-providing materials which are initially immobile in a photographic element or are ballasted overcome several of the problems with initially mobile compounds. The dyes could be temporarily ballasted by a heavy counter ion such as a barium salt as disclosed in Yutzy, U.S. Pat. No. 2,756,142 issued July 24, 1956. The dyes can contain a removable ballast group as described in Whitmore, Canadian Pat. No. 602,607 issued Aug. 2, 1960, U.S. Pat. Nos. 3,227,552 by Whitmore issued Jan. 4, 1966, 3,628,952, 3,728,113, 3,725,062, and the like. Compounds which undergo intramolecular ring closure upon oxidation to split off a dye are disclosed in U.S. Pat. Nos. 3,443,939, 3,443,940 and 3,443,941, all issued May 13, 1969, and 3,751,406 issued Aug. 7, 1973. Improved initially immobile compounds which undergo a redox reaction followed by alkali cleavage to split off a dye or dye precursor moiety are disclosed in Fleckenstein et al, U.S. Pat. No. 4,076,529 issued Feb. 28, 1978. However, these image dye-providing materials are generally limited in application by the fact that the dye is released in the areas where oxidation takes place. Thus, direct-positive silver halide emulsions or some other reversing mechanism, such as use of development nuclei in layers adjacent the recording layer, are used if a positive transfer image is desired.

Positive-working immobile compounds for use in photographic elements are the subject of our copending application, U.S. Ser. No. 534,966 filed Dec. 20, 1974. The positive-working compounds disclosed therein overcome many of the inherent limitations of the initially immobile compounds of the prior art. Generally, the compounds disclosed in our copending application are immobile ballasted compounds which can undergo a reaction such as a nucleophilic displacement reaction in their reduced form to release a mobile and diffusible photographically useful group, and said compounds can be oxidized, such as by a redox reaction in a photographic element, to lower substantially the rate of release of said photographically useful groups.

In certain embodiments where the positive-working immobile compounds are used, it is desirable to have more than one degree of control to monitor the release of the diffusible photographically useful moiety. We have found that compounds which contain at least two separate ballasted releasing groups attached to diffusible moieties provide some improved properties. In one particular embodiment, improved image quality is observed where the compounds remain in association with adjacent layers containing the released diffusible moiety subsequent to processing.

Generally, the compounds of this invention are immobile intramolecular nucleophilic displacement compounds and can be represented by the generic word formula:

(Ballast-(IND)Diffusible group wherein (IND) is an intramolecular nucleophilic displacement moiety, n is a positive integer of 2 or greater and is preferably 2, and the Diffusible group is a photographically useful group such as an image dye-providing material or a photographic reagent wherein said compound contains (1) an electrophilic cleavage group separating said Diffusible group from each said Ballast and (2) (IND) contains a nucleophilic group capable of undergoing intramolecular nucleophilic displacement with the electrophilic group connecting said (IND) to said diffusible group.

When the compounds are used in a photographic system, the nucleophilic group functions by reacting at the electrophilic center of the electrophilic cleavage group, displacing the ballast moiety from the photographically useful group of the compound. The photographically useful group upon release from the ballast moieties can then diffuse within the immediate layer, to adjacent layers or to receiving layers where it can carry out its function in the system. However, where at least one of the nucleophilic groups is oxidized, such as by redox reaction with an oxidized silver halide developer, the electrophilic group remains substantially unaffected by the oxidized nucleophilic group and the photographically useful group remains immobile and nondiffusible in its initial location.

In one embodiment, this invention relates to new organic compounds which comprise (1) at least two oxidizable nucleophilic groups and (2) at least two electrophilic cleavage groups linking a photographically useful group such as an image dye-providing group and two separate groups, each of which serves as a ballast to render said photographically useful group immobile in a photographic element. In certain highly preferred embodiments, the compounds contain two separate 2,1-benzisoxazolone nuclei.

In a specific embodiment in accordance with this invention, a photographic film unit is provided which is adapted to be processed by passing said unit between a pair of juxtaposed pressure-applying members, such as would be found in a camera designed for in-camera processing. The unit comprises (1) a photosensitive element which contains a silver halide emulsion having associated therewith an immobile, intramolecular nucleophilic displacement compound as designated above, (2) an image dye-receiving layer, (3) means for discharging an alkaline processing composition within the film unit such as a rupturable container which is adapted to be positioned during processing of the film so that a compressive force applied to the container by the pressure-applying members will effect a discharge of the container's contents within the film, and (4) a silver halide developing agent which is soluble in alkaline processing composition located within said film unit.

In a highly preferred embodiment, this invention relates to a photographic transfer process comprising:
(a) treating a photographic element prepared in accordance with this invention with an alkaline processing composition in the presence of a silver halide developing agent to effect development of each of the exposed silver halide emulsion layers, thereby oxidizing the developing agent;
(b) the oxidized developing agent cross-oxidizing said immobile compound according to this invention as a function of development before substantial release of said photographically useful group occurs whereby said cross-oxidation substantially reduces the rate of release of said photographically useful group;
(c) maintaining said photographic elememt in an alkaline medium for a time sufficient to release said photographically useful group from the immobile compound which has not reacted with said developing agent; and
(d) at least a portion of said photographically useful compound providing a positive image record.

In this embodiment, the photographically useful compound is preferably an image dye or image-dye precursor. The image-transfer process is preferably carried out in an integral negative receiver image-transfer film unit where the image-receiving layer and the photographic recording layers are coated on the same support, preferably with an opague layer and a layer which is reflective to light located between the receiver layer and the recording layers; the alkaline processing composition can be applied between the outer recording layers of the photographic element and a cover sheet which can be transparent and superposed before exposure.

The compounds of this invention exhibit particularly improved results when employed in integral negative receiver film units, especially where the layers of the film unit are not substantially dry within a day. The compounds of this invention appear to reduce contamination which may be due to incidental release of dye from compounds remaining in the negative portion of the film unit before layers of the film unit are dried. Moreover, the present compounds appear to provide for better control of unwanted dye transfer in the minimum density areas of the image record for each respective dye when used as the image dye-providing material in image-transfer processes and film units.

Positive retained images can also be readily obtained in photographic elements of this invention, and especially those elements which contain an immobile compound in accordance with this invention which contains an image dye or dye precursor and a hydrolyzable precursor for a nucleophilic group. The elements can be first developed with a developing agent in an environment having a pH below that necessary to hydrolyze the precursor for said nucleophilic group; then the photographic element can be fogged, light-flashed, etc., and developed in a solution having a pH sufficiently high to effect intramolecular nucleophilic displacement of said immobile compounds.

Generally, the immobile compounds contain a nucleophilic group and an electrophilic group so chosen that, when the compound is incorporated into a photographic element, the rate of oxidation of the nucleophilic group is substantially greater than the rate of intramolecular nucleophilic displacement or cleavage at the electrophilic group. Since the rate of oxidation is substantially greater than the rate of nucleophilic displacement, an imagewise pattern of a more mobile group can be produced after displacement; i.e., where said compound contains an image dye which is diffusible after nucleophilic displacement, the image dye can diffuse to layers adjacent the layer of initial location of said compound. Generally, there will be at least twice as much and preferably at least ten times more of said nucleophilic displacement in the unoxidized areas than in the oxidized areas during the development and image-forming process, and preferably there is substantially no nucleophilic displacement in the areas of said photographic element where all of said compound is oxidized. Where dyes or dye precursors are released, generally at least two times and preferably at least five times more dye or dye precursor is released in the unoxidized areas than in the oxidized areas.

In certain highly preferred embodiments, the compounds of this invention contain a group which a precursor for the oxidizable nucleophilic group, for example, a hydrolyzable precursor for an hydroxylamine group. In compounds where the nucleophilic group is blocked, the possibility of premature reactions" releasing the photographically useful moiety is substantially eliminated. Moreover, by controlling the development conditions, the availability of the nucleophilic group for reaction and intramolecular nucleophilic displacement can be delayed, if desired.

In certain embodiments, the compounds useful in accordance with this invention have the following structure:

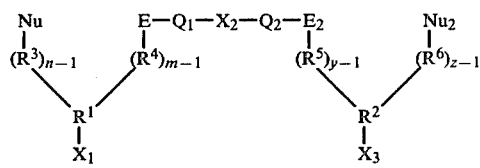

wherein $R^1$ and $R^2$ are each an acyclic organic group or preferably a cyclic organic group including bridged-ring groups, polycyclic groups and the like, which preferably have from 5–7 members in the ring to which Nu and E and $Nu_2$ and $E_2$ are attached, and more preferably an aromatic ring, such as a carbocyclic ring, e.g., benzenoid groups, etc., or a heterocyclic ring, including fused rings, substituted aromatic rings the like, the preferably $R^1$ and $R^2$ each contain less than 50 atoms and more preferably less than 15 atoms; $R^3$, $R^4$, $R^5$ and $R^6$ are bivalent organic groups containing from 1–3 atoms in the bivalent linkage and can be alkylene groups, oxalkylene, thialkylene and the like, including large groups in side chains on said linkage which can function as a ballast, e.g., groups containing at least 8 carbon atoms, provided said group preferably contains a carbon atom covalently bonded to E and $E_2$ respectively; Nu and $Nu_2$ are each an oxidizable nucleophilic group or a precursor for an oxidizable nucleophilic group including precursors such as hydrolyzable cyclic group formed together with substituents on $R^1$ and $R^2$ respectively, with useful oxidizable nucleophilic groups including, for example, a hydrazine group:

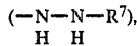

an hydroxyamino group:

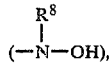

including an alkali-labile or hydrolyzable precursor for an hydroxyamino group such as:

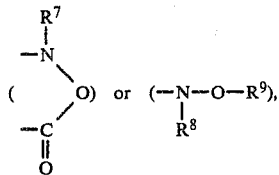

an hydroxy group (—OH) including precursors for an hydroxy group such as (—O—$R^9$), a sulfonamido group, a primary amino group (—$NH_2$) including precursors for a primary amino group, such as:

wherein $R^1$ and $R^2$ are preferably an aromatic carbocyclic ring containing at least one amino or hydroxy group in an ortho or para position to Nu and $Nu_2$ and m is 1 when Nu or $Nu_2$ are an hydroxy group or a primary amino group; $R^9$ can be an alkali-labile group or hydrolyzable group such as an acyl group comprising from 2-10 carbon atoms; $R^7$ is an alkyl group having from 1-10 carbon atoms including substituted alkyl groups, an aryl group having from 6-20 carbon atoms including substituted aryl groups or a group mentioned for $R^9$; and $R^8$ can be a hydrogen atom or any group useful for $R^7$; E and $E_2$ are each an electrophilic group and preferably a carbonyl group, including carbonyl (—CO—) and thiocarbonyl (—CS—), or it can be a sulfonyl group (—$SO_2$—); $Q_1$ and $Q_2$ are each a bivalent group providing a mono atom linkage between E and $X_2$ and between $E_2$ and $X_2$ wherein said mono atom is a nonmetallic atom of group VA or VIA of the periodic table in its -2 or -3 valence state, such as a nitrogen atom, an oxygen atom, a sulfur atom, a selenium atom and the like, wherein said atom provides the two covalent bonds linking $X_2$ to E and $X_2$ to $E_2$ respectively, and when it is a trivalent atom it can be monosubstituted with a hydrogen atom, an alkyl group containing from 1-20 atoms and preferably 1-10 carbon atoms, including substituted carbon atoms and carbocyclic groups, or an aryl group containing from 6-20 carbon atoms including substituted aryl groups; $X_1$ and $X_3$ are a ballasting group of sufficient size to render $Q_1$-$X_2$-$Q_2$ immobile in an alkali-permeable layer of a photographic element, and $Q_1$-$X_2$-$Q_2$ is a photographically useful moiety such as an image dye, an image-dye precursor, or a photographic reagent such as an antifoggant moiety, a toner moiety, a fixing agent, a development accelerator, a developing-agent moiety, a hardener moiety, and the like, including the necessary linking groups to attach the respective moiety to E or $E_2$; n, m, y and z are positive integers of 1 or 2; and $R^1$, $R^2$, $R^3$, $R^4$, $R^5$ and $R^6$ are selected to provide substantial proximity of Nu to E and $Nu_2$ to $E_2$ to permit intramolecular nucleophilic cleavage of $Q_1$ from E and $Q_2$ from $E_2$ and are preferably selected to provide 1 to 3 to 5 atoms between the atom which is the nucleophilic center of said nucleophilic group and the atom which is the electrophilic center, whereby said compound is capable of forming a 3- or 5- to 7-membered ring and most preferably a 5-or 6-membered ring upon intramolecular nucleophilic displacement of the group $Q_1$-$X_2$-$Q_2$ from said electrophilic groups.

In the above formula where $Q_1$-$X_2$-$Q_2$ is a photographic reagent, a photographically active group can be made available by $Q_1$ or $Q_2$ upon cleavage of $Q_1$-$X_2$-$Q_2$ from the remainder of the compound, i.e., such as where $Q_1$-$X_2$-$Q_2$ forms a mercaptotetrazole and the like. It is also understood that the photographically useful moiety represented by $Q_1$-$X_2$-$Q_2$ can be present in the photographic element in either the ionized or unionized forms after release of the ballast portions of the compound; i.e., when $Q_1$-$X_2$-$Q_2$ is displaced from the remainder of the compound, it can be in its ionic form when above the pKa of the compound or in its nonionic or salt forms below the pKa.

The nature of the ballasting groups in the above compounds is not critical as long as the portion or the compound on the ballast side of E and $E_2$ will render $Q_1$-$X_2$-$Q_2$ immobile; $Q_1$-$X_2$-$Q_2$ generally contains sufficient solubilizing groups to render it mobile and diffusible in an alkaline medium after cleavage. Thus, $X_1$ or $X_3$ could each be a hydrogen atom if $R^1$, $R^2$ and $R^3$ or $R^4$, $R^5$ and $R^6$ respectively confer sufficient insolubility to the compound to render it immobile, especially where $R^3$, $R^4$, $R^5$ and $R^6$ include large side chains containing from about 8-20 carbon atoms. However, $X_1$ or $X_2$ generally comprise long-chain alkyl radicals, as well as aromatic radicals of the benzene and naphthalene series. Typical, useful groups for the ballast function contain at least 8 carbon atoms and preferably at least 14 carbon atoms.

Generally, the major portion of the ballast group such as the alkyl group is attached to $R^1$ or $R^2$ through a convenient connecting group for synthesis, such as a sulfonyl group, a sulfamoyl group, an ether group, a carbamoyl group and the like, to provide a ballast which is an alkylsulfonyl, an alkylsulfamoyl, an alkylether, an alkylcarbamoyl and the like. Details of compounds having these types of ballast groups are disclosed in U.S. Ser. No. 534,966 which is incorporated herein by reference.

In certain embodiments, the ballast group of the compounds of the above formulae contains a base-ionizable group to improve the photographic performance of the compounds, especially when the photographic element containing the compounds is processed in an aqueous medium under alkaline conditions. While the compounds remain immobile in the element because of their size or molecular configuration, base-ionizable groups appear to improve reactivity, including groups appended to the ballast chain, such as carboxyl groups, sulfonic acid groups and the like, or those intralinear groups in the ballast chain, such as sulfonamido groups and the like.

The term "nucleophilic group" as used herein refers to an atom or group of atoms which have an electron pair capable of forming a covalent bond. Groups of this type are sometimes ionizable groups which react as anionic groups. The term "oxidizable nucleophilic group" refers to that nucleophilic group which can be oxidized, thus causing a substantial reduction in the rate of intramolecular nucleophilic displacement relative to the electrophilic group. Generally, the groups are less nucleophilic in character upon oxidation or have a structure which adversely affects the proximity of the nucleophilic center with respect to the electrophilic center.

The nucleophilic group can contain only one nucleophilic center such as the oxygen atom in an hydroxy group, or it can contain more than one nucleophilic center such as in the case of an hydroxylamine group where either the nitrogen atom or the oxygen atom can be the nucleophilic center. Where more than one nucleophilic center is present in the nucleophilic group on the intramolecular nucleophilic displacement compounds of this invention, the nucleophilic attack and displacement will generally occur through the center which is capable of forming the most favored ring structure; i.e., if the oxygen atom of the hydroxylamine group would form a 7-membered ring and the nitrogen atom would form a 6-membered ring, the active nucleophilic center would generally be the nitrogen atom.

The term "electrophilic group" refers to an atom or group of atoms which are capable of accepting an electron pair to form a covalent bond. Typical electrophilic groups are sulfonyl groups ($-SO_2-$), carbonyl grops such as carbonyl ($-CO-$) and thiocarbonyl ($-CS-$), and the like, whee the carbon atom of the carbonyl group forms the electrophilic center of the group and can sustain a partial positive charge. The term "electrophilic cleavage group" is used herein to refer to groups (-E-$Q_1$-) and (-$E_2$-$Q_2$-) wherein E and $E_2$ are electrophilic groups and $Q_1$ and $Q_2$ are bivalent leaving groups providing a mono atom linkage between E and $X_2$ and $E_2$ and $X_2$ wherein said mono atom is a nonmetallic atom which has a negative valence of 2 or 3. The leaving group is capable of accepting a pair of electrons upon being released from the electrophilic group. Where the nonmetallic atom is a trivalent atom, it can be monosubstituted by a group which can be a hydrogen atom, an alkyl group including substituted alkyl groups and cycloalkyl groups, or an aryl group including substituted aryl groups. Typical atoms useful for $Q_1$ and $Q_2$ are the nonmetallic atoms in groups VA and VIA of the periodic table which are capable of having a negative valence of 2 or 3, such as nitrogen atoms, sulfur atoms, oxygen atoms, selenium atoms and the like.

Generally, the compounds of this invention are defined as intramolecular nucleophilic displacement compounds. The term "intramolecular nucleophilic displacement" is understood to refer to a reaction in which a nucleophilic center attached to a compound reacts at another site on said compound, which is an electrophilic center, to effect displacement of a group or atom attached to said electrophilic center. Generally, the intramolecular nucleophilic displacement compounds are those compounds which have the nucleophilic group and the electrophilic center juxtaposed by the three-dimensional configuration of the molecule to promote close proximity of the groups whereby the reaction can take place. Generally, the respective electrophilic and nucleophilic groups can be put on any compound where the groups are held in the possible reaction positions, including polymeric compounds, macrocyclic compound, polycyclic compounds, enzyme-like structures and the like. However, the nucleophilic groups and electrophilic groups are preferably located on compounds wherein a cyclic organic ring or a transient cyclic organic ring can be easily formed by intramolecular reaction of the nucleophilic group at the electrophilic center. Cyclic groups can be generally formed with 3-7 atoms thereon, and preferably in accordance with this invention the nucleophilic group and the electrophilic group are positioned on a compound where they can form a 3- or 5-to 7-membered ring, and more preferably a 5- or 6-membered ring (4-membered rings are generally known to be difficult to form in organic reactions). Intramolecular nucleophilic displacement occurs with the compounds of this invention when the compound is in the reduced state and the rate of nucleophilic displacement appears to be substantially reduced and preferably eliminated when the nucleophile is oxidized. The mechanism of the above compounds as described is believed to be different in kind from compounds known in the art which are oxidized to provide an electrophilic center with subsequent intramolecular reaction followed by release of a dye.

The compounds of this invention preferably contain the nucleophilic groups and the electrophilic cleavage groups connected through a linkage which can be acyclic, but is preferably a cyclic group to provide more favorable juxtaposition of the groups whereby intramolecular nucleophilic attack on the electrophilic center is favored. In certainly highly preferred embodiments, the nucleophilic group and the electrophilic group are both attached to the same aromatic ring structure, which can be a carbocyclic ring structure or a heterocyclic ring structure and includes fused rings wherein each group can be on a different ring; preferably, both groups are attached directly to the same aromatic ring, which is preferably a carbocyclic ring structure.

In certain embodiments, the compounds of this invention contain from 1 to about 5 atoms and preferably 3 or 4 atoms between the nucleophilic center of the oxidizable nucleophilic group and the atom which forms the electrophilic center, whereby the nucleophilic center, taken together with the center of the electrophilic group, is capable of forming a ring or a transient ring having from 3 to 7 atoms therein and preferably 5 or 6 atoms therein.

The intramolecular nucleophilic displacement compounds of this invention can contain electron-withdrawing or electron-donating substitutents to alter the rate of reaction of the compound. In one highly preferred embodiment, electron-withdrawing groups are located on the cyclic groups represented by $R^1$ and $R^2$ to improve the reaction rates when the compound is used to release dye in an image-transfer film unit. In one preferred embodiment, $X_1$ and $X_3$ are attached to $R^1$ and $R^2$ respectively through an electron-withdrawing group such as a sulfo group includin a sulfonamide, a sulfone, and the like.

The term "nondiffusing" used herein has the meaning commonly applied to the term in photography and denotes materials which for all practical purposes do not migrate or wander through organic colloid layers in an alkaline medium, such as gelatin, in the photographic elements of the invention. The same meaning is to be attached to the term "immobile".

The term "diffusible" as applied to the materials of this invention denotes materials having the property of diffusing effectively through the colloid layers of the photographic elements in an alkaline medium in the presence of "nondiffusing" materials. "Mobile" has the same meaning.

In one highly preferred embodiment, the immobile compounds of this invention comprise a 2,1-benzisoxazolone compound linked to a photographically useful moiety such as a dye or dye precursor. The dye can be connected to the benzisoxazolone moiety through an electrophilic cleavage group or it can be attached directly to the benzisoxazolone moiety with the provision that a ballast group is attached to the benzisoxazolone moiety through the electrophilic cleavage group. Certain preferred compounds can be represented by the formula:

$R^4$, $L^5$ and $R^6$ are additionally characterized as being bivalent groups containing from 1 to 2 atoms in the bivalent linkage and wherein n, m, y and Z are preferably 1, $Q_1$-$X_2$-$Q_2$ is preferably a dye or dye precursor including the necessary linking groups for synthesis to attach the dye or dye precursor to E and $E_2$; E and $E_2$ are each preferably a carbonyl group; and $Q_1$ and $Q_2$ comprise a bivalent group containing a nitrogen atom linking E to $X_2$ and $E_2$ to $X_2$. The benzene ring can, of course, contain additional substituents such as electron-withdrawing groups or electron-donating groups groups to provide changes in the resonance of the compound, thus providing for variations in reaction rates.

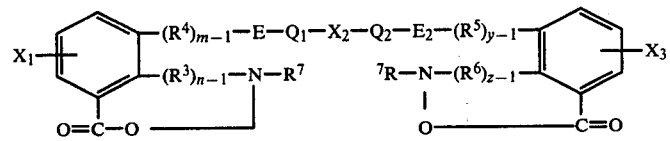

wherein $X_1$, $X_2$, $X_3$, E, $E_2$, $Q_1$, $Q_2$, $R^3$, $R^4$, $R^5$, $R^6$, n, m, y z and each $R^7$ are as defined above, and wherein $R^3$, Typical useful benzisoxazolone compounds are as follows:

Compound I
(magenta)

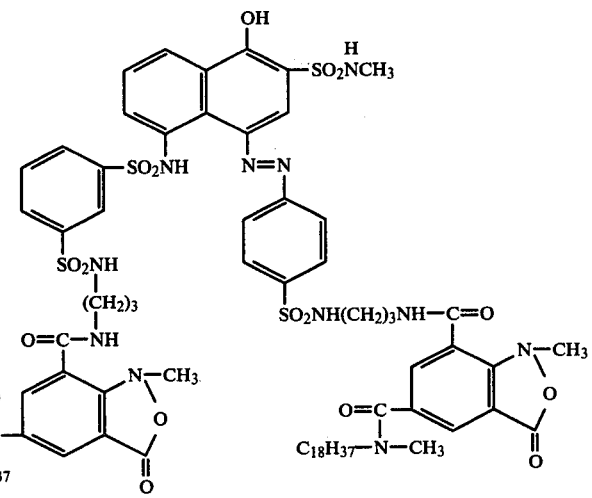

Compound II
(shifted yellow)

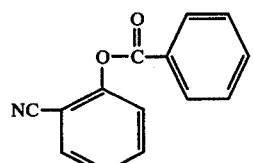

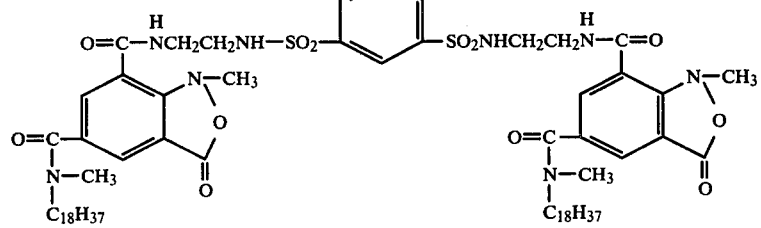

Compound III
(magenta)

-continued
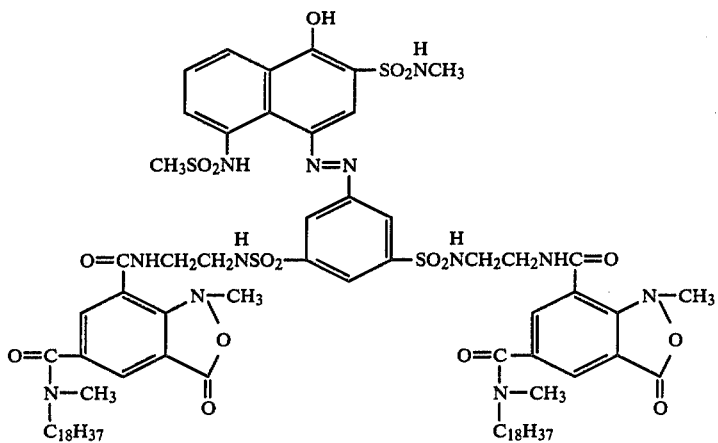
Compound IV
(magenta)
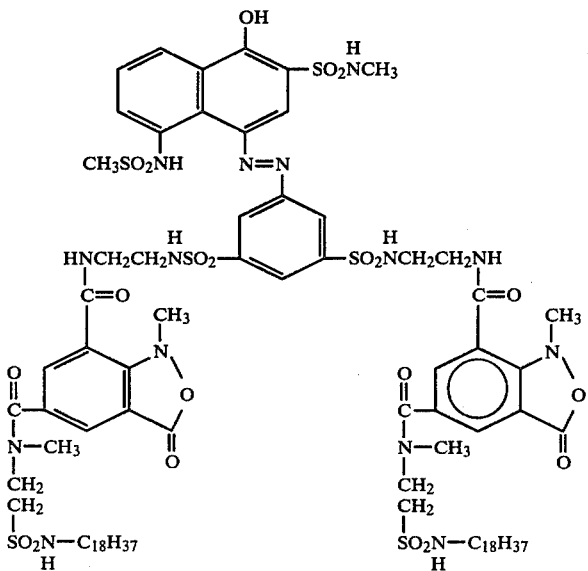
Compound V
(shifted magenta)

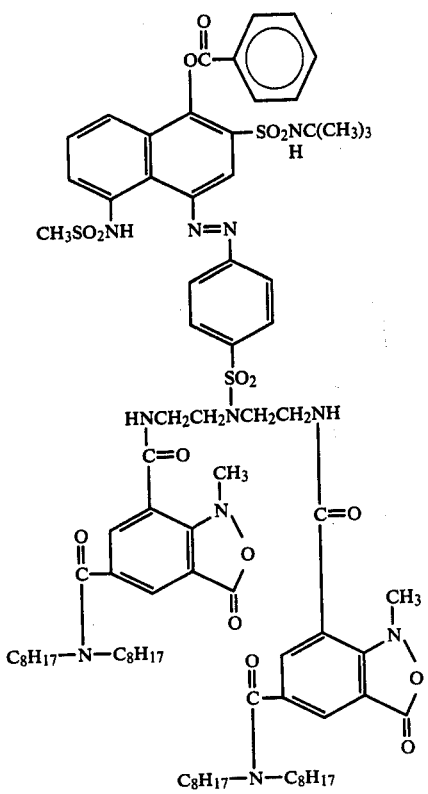
Compound VI
(shifted magenta)
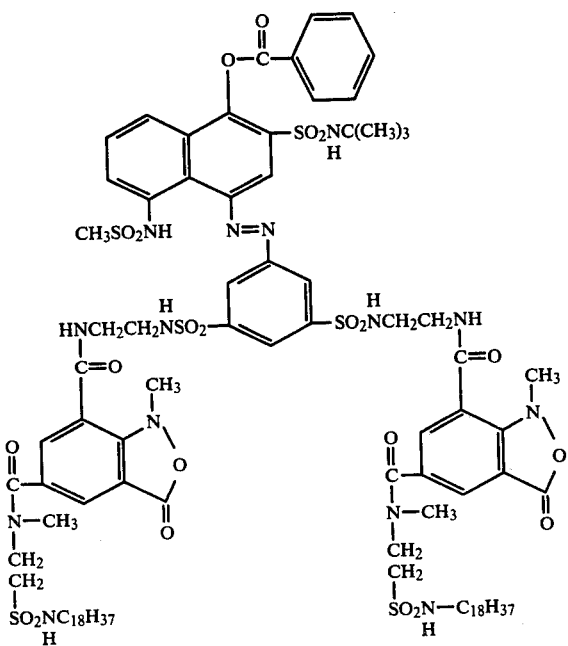
Compound VII
(shifted magenta)

-continued
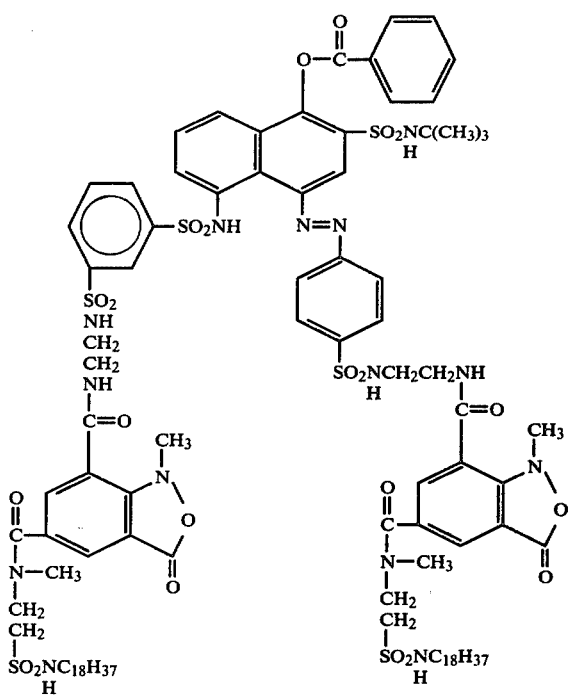
Compound VIII
(shifted magenta)
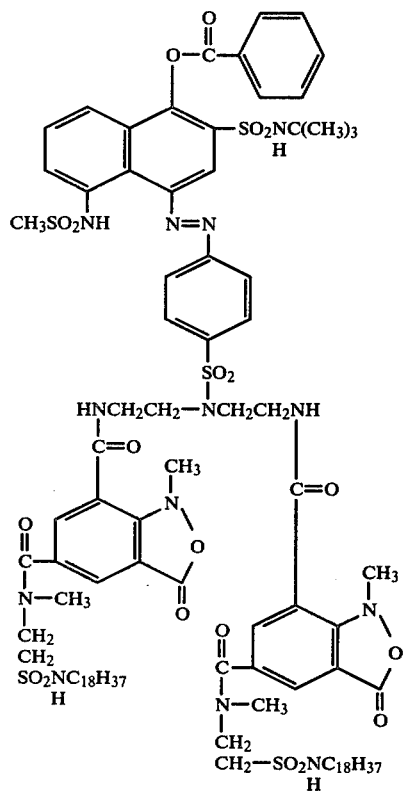
Compound IX
(magenta)

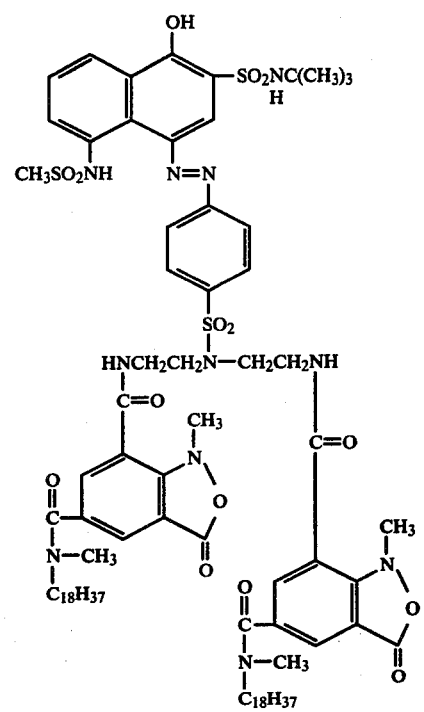
Compound X
(shifted magenta)
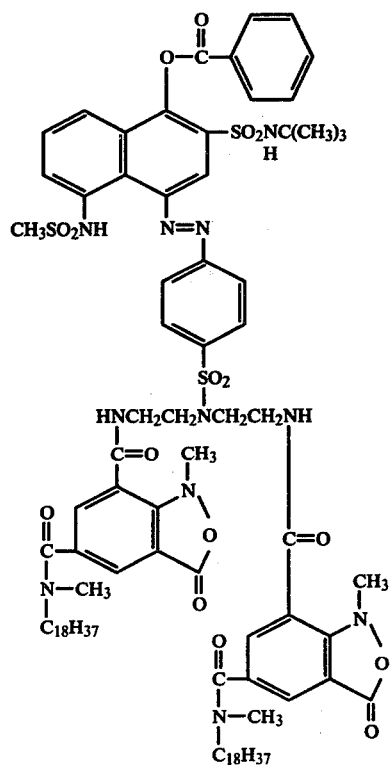
Compound XI
(magenta)

-continued
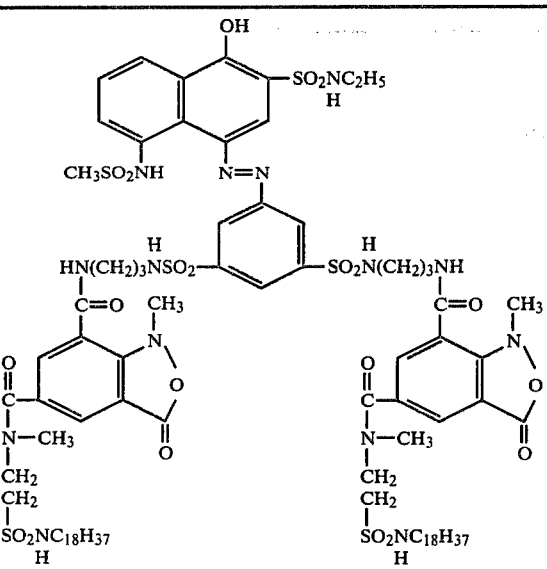
Compound XII
(shifted magenta)
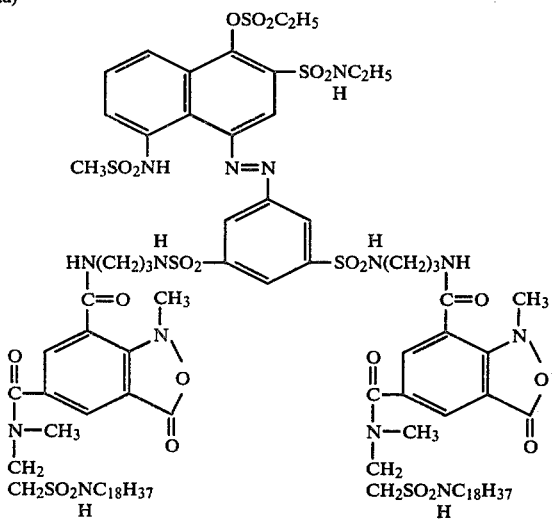
Compound XIII
(shifted magenta)
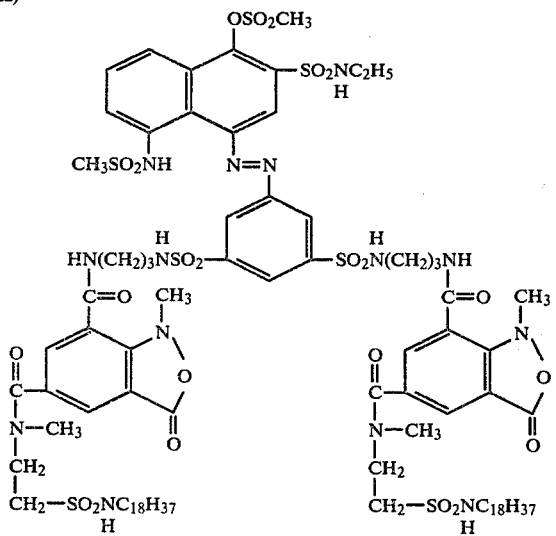
Compound XIV
(shifted yellow)

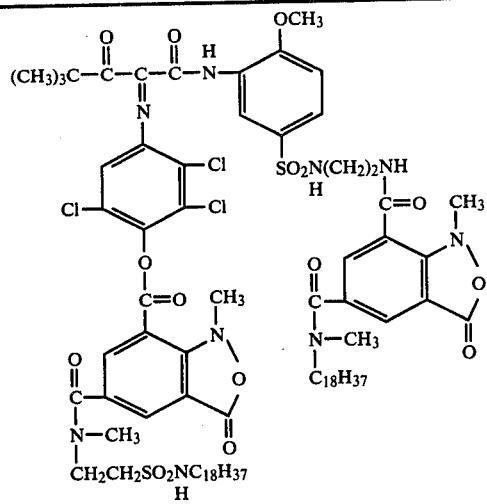
Compound XV
(cyan)
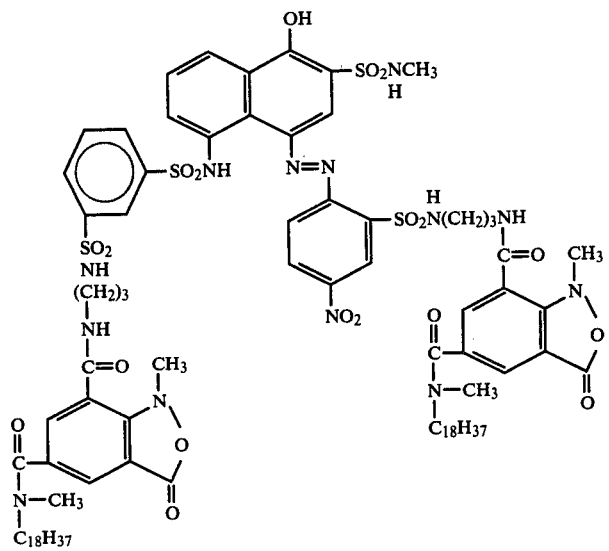
Compound XVI
(cyan)
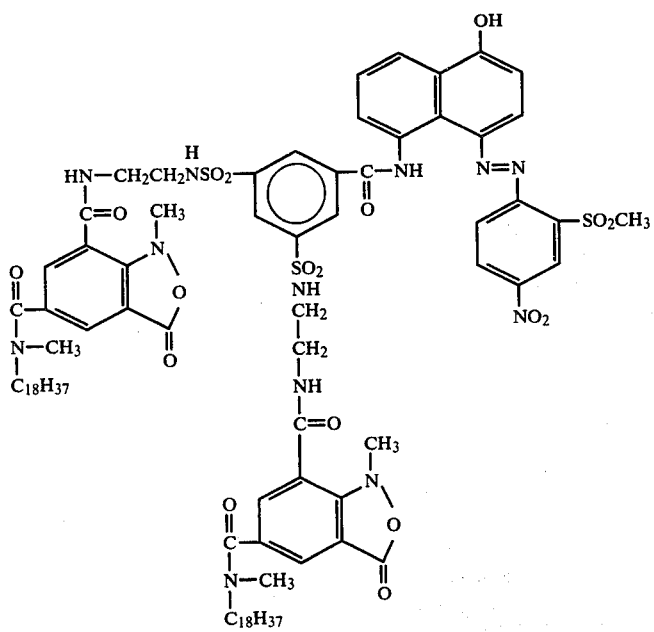
Compound XVII (shifted cyan)

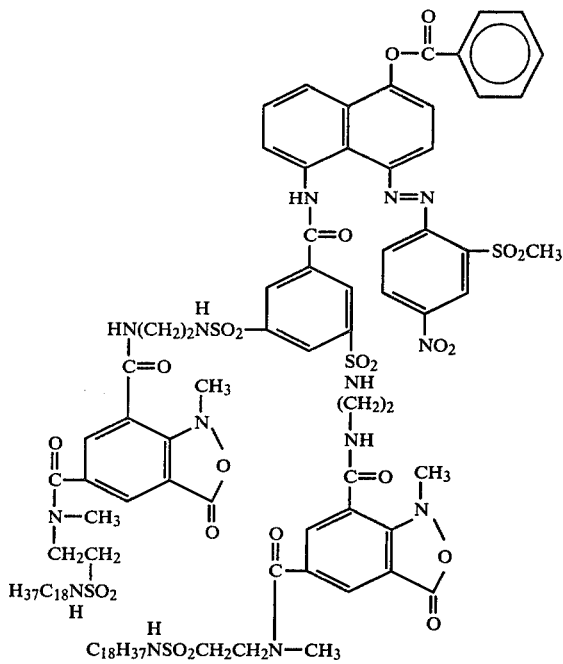

The photographic processes using the immobile compounds are generally carried out in an alkaline medium wherein the nucleophilic displacement can easily take place. In certain embodiments, the processes are carried out in an alkaline medium having a pH of above 12; at a high pH silver halide development proceeds rapidly, dye mobility is generally high, and the like. High-pH conditions are especially preferred for image-transfer processes using the compounds of this invention. Moreover, when the 2,1-benzisoxazolone compounds as described above are used in photographic elements, they are generally contacted with an alkaline solution at a pH sufficiently high to hydrolyze the isoxazolone ring to form an hydroxylamino group. The compound can then react with an oxidized silver halide developer to reduce the rate of release of the photographically useful group; however, where the compound remains unoxidized, the photographically useful group is released.

The compounds of this invention can generally be prepared by using conventional techniques used in organic chemistry with proper selection of the starting materials. The photographically useful group can be synthesized by methods known in the art with the appropriate linkages and groups for reaction with the remainder of the compound. The examples define a typical preferred procedure where the acid chloride of a 2,1-benzisoxazolin-3-one is reacted with a dye with an amine group thereon to produce compounds in accordance with this invention.

The 1,2-benzisoxazolone intermediate can be made by several procedures. In one exemplary procedure, o-nitrobenzoic acid derivatives can be reduced electrochemically in acidic media to the corresponding hydroxylamino compounds with concomitant acid-catalyzed ring-closure reaction. The electrochemical reduction can be carried out using a mercury working electrode when working on small scales, and preferably when working at large scales a cathode having a low hydrogen overvoltage is preferred such as platinum, graphite, stainless steel, nickel, copper, chromium, silver and the like. In another exemplary procedure, the o-nitrobenzoic acids are reduced by a catalytic hydrogenation process using a platinum dioxide or rhodium catalyst. In a preferred exemplary procedure, the o-nitrobenzoic acids are reduced by chemical reducing agents such as zinc, tin, stannous chloride, etc., under appropriate conditions.

In certain preferred embodiments, the compounds of this invention comprise a moiety which is an image dye-providing material. Preferably, the image dye-providing moiety is a preformed dye or a shifted dye. Dye materials of this type are well-known in the art and include dyes such as azo dyes, azomethine (imine) dyes, anthraquinone dyes, alizarin dyes, merocyanine dyes, quinoline dyes, cyanine dyes, metallized dyes, metallizable dyes, and the like. The shifted dyes include those compounds wherein the light absorption characteristics are shifted hypsochromically or bathochromically when subjected to a different environment such as a change in pH, reaction with a material to form a complex, tautomerization, reactions to change the pKa of the compound, removal of a group such as a hydrolyzable acyl group connected to an atom of the chromophore as mentioned in Weyerts, U.S. Pat. No. 3,260,597 issued July 12, 1966, and the like. In certain embodiments, the shifted dyes are highly preferred and especially those containing a hydrolyzable group on an atom affecting the chromophore resonance structure, since the compounds can be incorporated directly in a silver halide emulsion layer or even on the exposure side thereof without substantial reduction in the recording light exposure. After exposure, the dye can be shifted to the appropriate color such as, for example, by hydrolytic removal of the acyl group to provide the respective image dye.

In another embodiment, the compounds of this invention contain a moiety which is an image-dye precursor. The term "image-dye precursor" is understood to refer to those compounds which undergo reactions encountered in a photographic imaging system to produce an image dye, such as color couplers, oxichromic compounds, and the like.

The compounds described herein have particular application in a diffusion transfer process where it is desired to have a dye entity transferred to an adjacent layer or a receiving element. However, in certain embodiments this invention relates to the release of an imagewise distribution of a diffusible photographically useful compound which is a photographic reagent. Typical useful photographic reagents are known in the art, such as in U.S. Pat. Nos. 3,227,551, 3,698,898, 3,379,529 and 3,364,022, for example, a silver complexing agent, a silver halide solvent, a fixing agent, a toner, a hardener, an antifoggant, a fogging agent, a sensitizer, a desensitizer, a developer or an oxidizing agent. In other words, $Q-X_2-Q_2$ in the above formula may represent any moiety which, in combination with one or more hydrogen atoms, provides a photographic reagent upon cleavage.

Typical useful compounds containing photographic reagents are as follows:

strained in the low-exposure toe as seen on the H and D curve, but not in the more fully exposed shoulder as seen on the H and D curve. Development inhibition of the unexposed areas is thereby achieved selectively. When the silver halide emulsions also have dye releasers in accordance with this invention associated therewith, the overall effect of the inhibitor or antifoggant is to release more dye in the unexposed regions, improving maximum image dye density to the image-receiving layer without increasing the amount of dye released in the exposed regions.

The photographically useful moiety represented by $Q_1-X_2-Q_2$ can also be a silver halide development accelerator such as a benzyl alcohol, a benzyl α-picolinium bromide and the like, a foggant including hydrazines and hydrazides such as an acetylphenylhydrazine and the like, or an auxiliary developer such as a hydroquinone, a 1-phenyl-3-pyrazolidone, an ascorbic acid and the like. When these compounds are used in photographic elements in association with silver halide emulsions which also have associated therewith image dye-providing materials in accordance with this invention, the released dye density of all dyes in the unexposed regions would be somewhat reduced by fog development. If, however, one layer was unexposed while the other two were given an imagewise exposure, the

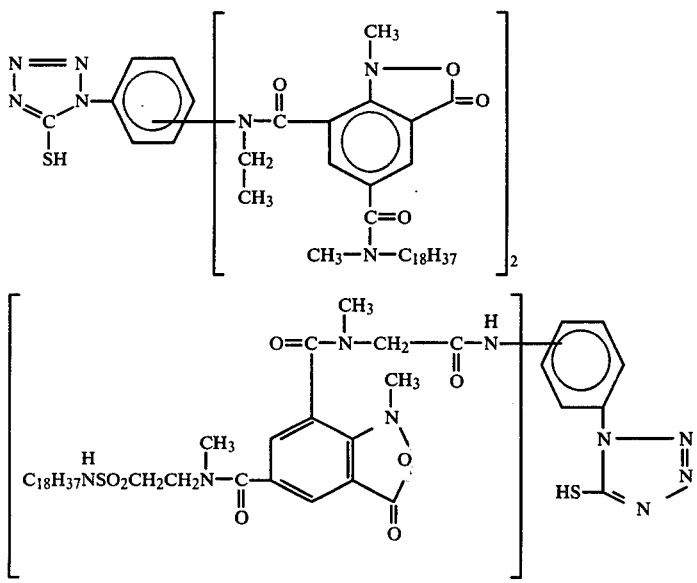

The photographically useful moiety represented by $Q_1-X_2-Q_2$ in the above general formula can be a silver halide development inhibitor including triazoles and tetrazoles such as a 5-mercapto-1-phenyltetrazole, a 5-methylbenzotriazole, a 4,5-dichlorobenzotriazole and the like, and it can also be an antifoggant including azaindenes such as a tetrazaindene and the like. The compounds which contain releasable silver halide development inhibitors or antifoggants can generally be used in the photographic elements in association with silver halide layers wherein said compound can be incorporated in amounts such as 1 to 100 mg./ft.$^2$ dissolved in a coupler solvent such as diethyl lauramide. When these compounds are incorporated in photographic elements in association with negative silver halide emulsions, a positive imagewise distribution of inhibitor or antifoggant will be produced upon development. Thus, silver development is inhibited or reamount of foggant or development accelerator reaching the unexposed layer from the other two layers would be less where those layers were exposed. Hence, the Dmax of the unexposed layer would increase as a function of exposure of the other two layers. This greatly enhances the saturation of single colors in a photograph.

When color couplers are present in the compounds of this invention, the coupler can be released in areas where no development occurs and can diffuse to an adjacent layer where they can be reacted with an oxidized color developer such as a primary aromatic amine to form the image dye. Generally, the color coupler and the color developer are so chosen that the reaction product is immobile. Typical useful color couplers include the pyrazolone couplers, pyrazolotriazole couplers, open-chain ketomethylene couplers, phenolic couplers and the like. Further reference to the description of appropriate couplers is found in Marchant, U.S. Pat. No. 3,620,747 issued Nov. 16, 1971, which is incorporated herein by reference.

The compounds of this invention containing oxichromic moieties can also be advantageously used in a photographic system since they are generally colorless materials due to the absence of an image-dye chromophore. Thus, they can also be used directly in the photographic emulsion or on the exposure side thereof without competitive absorption. Compounds of this type are those compounds which undergo chromogenic oxidation to form the respective image dye. The oxidation can be carried out by aerial oxidation, incorporation of oxidants into the photographic element or film unit, or use of an oxidant during processing. Compounds of this type have been referred to in the art as leuco compounds, i.e., compounds which have no color. Typical useful oxichromic compounds include leuco indoanilines, leuco indophenols, leuco anthraquinones and the like. In certain preferred embodiments, the compounds of this invention contain oxichromic moieties as described in Lestina and Bush, U.S. Pat. No. 3,880,658 issued Apr. 29, 1975, which is incorporated herein by reference.

The compounds of this invention are particularly useful in photographic elements and in photographic processes to provide an imagewise distribution of a photographically useful compound. The photographic element can contain the immobile compounds in association with any photographic material which produces an oxidation product during development which in turn can react with the nucleophilic group on said compound. In certain preferred embodiments, where silver halide emulsions are used as the recording means, the emulsion can be a negative, direct-positive or reversal emulsion and the like which undergo development with a silver halide developing agent to produce oxidized silver halide developer. The oxidized silver halide developing agent can react with the nucelophilic group to produce an addition product and the like, but preferably the silver halide developing agent is so chosen that a simple redox reaction takes place to reduce substantially the rate of release of the photographically useful moiety.

Black-and-white or one-color systems can be made which employ as few as one silver halide emulsion and compounds according to this invention which comprise the required image dye-providing moieties to provide the desired net color effect. Preferably, the compounds of this invention are used in three-color systems such as, for example, photographic elements containing a layer comprising a red-sensitive silver halide emulsion having associated therewith an intramolecular nucleophilic displacement compound comprising a cyan image dye-providing moiety, a layer containing a green-sensitive silver halide emulsion having associated therewith an intramolecular nucleophilic displacement compound which comprises a magenta image dye-providing moiety, and a layer containing a blue-sensitive silver halide emulsion having associated therewith an intramolecular nucleophilic displacement compound which comprises a yellow image dye-providing moiety.

The photographic element can be designed to provide an image record in either the image dye-providing material released and made diffusible or in the immobile dye remaining in the initial location attached to the oxidized compound and associated with the respective photographic recording material or, in certain instances, both image records can be used. The residual nondiffusible dye can provide an image record which will be present as a function of silver halide development. The silver and silver halide remaining after development can be removed, if desired, to provide better color properties in the record.

In certain preferred embodiments, the photographic element is used in an image-transfer film unit where the dye image-providing material upon release diffuses to an adjacent image-receiving layer. The compounds of this invention can be used in any image-transfer unit format where either initially mobile compounds are used, such as dye developers, or where the initially immobile compounds are used, such as ballasted redox releasing compounds. Typical useful image-transfer formats are disclosed in U.S. Pat. Nos. 2,543,181, 2,661,293, 2,774,668, 2,983,606, 3,227,550, 3,227,552, 3,309,201, 3,415,644, 3,415,645, 3,415,646 and 3,635,707, Canadian Patent No. 674,082, Belgian Patent Nos. 757,959 and 757,960, both issued Apr. 23, 1971, and the like. However, the appropriate silver halide emulsions will have to be used in each format since the present compounds yield a positive image in diffusible dye with a negative recording and developing emulsion.

In certain embodiments, the photographic elements of this invention are processed in the presence of a silver halide developing agent which is preferably a silver halide developing agent which has a redox potential whereby it will cross-oxidize when oxidized with immobile compounds of this invention. Typical useful silver halide developers include hydroquinone compounds such as hydroquinone, 2,5-dichlorohydroquinone, 2-chlorohydroquinone and the like; aminophenol compounds such as 4-aminophenol, N-methylaminophenol, 3-methyl-4-aminophenol, 3,5-dibromoaminophenol and the like; catechol compounds such as catechol, 4-cyclohexylcatechol, 3-methoxycatechol, 4-(N-octadecylamino)catechol and the like; phenylenediamine compounds such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine and the like; 3-pyrazolidone compounds such as 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(3-chlorophenyl)-3-pyrazolidone, 1-(4-chlorophenyl)-3-pyrazolidone, 1-(4-tolyl)-4-methyl-3-pyrazolidone, 1-(2-tolyl)-4-methyl-3-pyrazolidone, 1(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone and the like; etc. A plurality of developing agents such as those disclosed in U.S. Pat. No. 3,039,869 can also be employed. Such developing agents can be employed in the liquid processing composition or may be contained, at least in part, in any layer or layers of the photographic element or film unit such as the silver halide emulsion layers, the dye image-providing material layers, interlayers, image-receiving layer, etc.

In highly preferred embodiments of this invention, the photographic element or film unit contains a compound in addition to said immobile compounds, which is an antifoggant or development restrainer which substantially prevents any further development of a silver halide emulsion after the initial imagewise development has occurred. Generally, the compound is one which will at least prevent fog buildup in a silver halide layer during the time necessary to release a substantial amount of the photographically useful group from the unoxidized compound. Typical useful development restrainer precursors which can be used to permit initial development but restrain development thereafter are disclosed in U.S. Pat. No. 3,260,597 by Weyerts, U.S. Ser. No. 367,306 by Hammond et al filed June 5, 1973, now abandoned, and the like. Conventional development restrainers can also be used in the photographic elements or film units wherein they are located in the processing composition, in layers adjacent the silver haldie emulsion layers, in the receiving element, in a cover sheet, etc., where contact with the silver halide emulsion is delayed until after the initial image-recording development has occurred.

In a photographic element according to the invention, each silver halide emulsion layer containing an image dye-providing material or having the image dye-providing material present in a contiguous layer may be separated from the other silver halide emulsion layers in the negative portion of the film unit by materials in addition to those described above, including gelatin, calcium alginate, or any of those disclosed in U.S. Pat. No. 3,384,483, polymeric materials such as polyvinylamides as disclosed in U.S. Pat. No. 3,421,892, or any of those disclosed in French Patent Nos. 2,028,236 or U.S. Pat. Nos. 2,992,104, 3,043,692, 3,044,873, 3,061,428, 3,069,263, 3,069,264, 3,121,011 and 3,427,158.

In certain preferred embodiments, the multicolor photographic elements of this invention contain interlayers containing antistain agents or oxidized developer scavengers, which interlayers are located between the respective color image-recording layers. Typical antistain agents or oxidized developer scavengers which aid in obtaining improved color separation are disclosed in U.S. Pat. Nos. 2,701,187, 3,700,453, 2,728,659, etc.

Generally speaking, except where noted otherwise, the silver halide emulsion layers in the invention comprise photosensitive silver halide dispersed in gelatin and are about 0.6 to 6 microns in thickness; the image dye-providing materials are dispersed in an aqueous alkaline solution-permeable polymeric binder, such as gelatin, in the same layer as the silver halide emulsion or as a separate layer about 1 to 7 microns in thickness; and the alkaline solution-permeable polymeric interlayers, e.g., gelatin, are about 1 to 5 microns in thickness. Of course, these thicknesses are approximate only and can be modified according to the product desired. In addition to gelatin, other suitable hydrophilic materials include both naturally occurring substances such as proteins, cellulose derivatives, polysaccharides such as dextran, gum arabic and the like; and synthetic polymeric substances such as water-soluble polyvinyl compounds like poly(vinylpyrrolidone), acrylamide polymers and the like.

The photographic emulsion layers and other layers of a photographic element employed in the practice of this invention can also contain, alone or in combination with hydrophilic, water-permeable colloids, other synthetic polymeric compounds such as dispersed vinyl compounds such as in latex form, and particularly those which increase the dimensional stability of the photographic materials. Suitable synthetic polymers include those described for example, in U.S. Pat. Nos. 3,142,568 by Nottorf issued July 28, 1964, 3,193,386 by White issued July 6, 1965, 3,062,674 by Houck et al issued Nov. 6, 1962, 3,220,844 by Houck et al issued Nov. 30, 1965, 3,287,289 by Ream et al issued Nov. 22, 1966, and 3,411,911 by Dykstra issued Nov. 19, 1968. Particularly effective are water-insoluble polymers of alkyl acrylates and methacrylates, acrylic acid, sulfoalkyl acrylates or methacrylates, those which have cross-linking sites which facilitate hardening or curing, and those having recurring sulfobetaine units as described in Dykstra, Canadian Patent No. 774,054.

Any material can be employed as the image-receiving layer in the film units of this invention as long as the desired function of mordanting or otherwise fixing the image dyes will be obtained. The particular material chosen will, of course, depend upon the dye image to be mordanted as mentioned hereinbefore.

Use of a pH-lowering layer in the film units of the invention will usually increase the stability of the transferred image. Generally, th pH-lowering layer will effect a reduction in the pH of the image layer from about 13 or 14 to at least 11 and preferably 5-8 within a short time after imbibition. For example, polymeric acids as disclosed in U.S. Pat. Nos. 3,362,819 issued Jan. 9, 1968, 2,584,030 issued Jan. 29, 1952, or 2,548,575 issued Apr. 10, 1951, or Belgian Patent No. 603,747 issued May 31, 1961, p. 47, may be employed. Such polymeric acids reduce the pH of the film unit after development to terminate development and substantially reduce further dye transfer and thus stabilize the dye image. Such polymeric acids comprise polymers containing acid groups, such as carboxylic acid and sulfonic acid groups, which are capable of forming salts with alkali metals, such as sodium or potassium, or with organic bases, particularly quaternary ammonium bases, such as tetramethyl ammonium hydroxide. The polymers can also contain potentially acid-yielding groups such as anhydrides or lactones or other groups which are capable of reacting with bases to capture and retain them. Generally, the most useful polymeric acids contain free carboxyl groups, being insoluble in water in the free acid form and which form water-soluble sodium and/or potassium salts. Examples of such polymeric acids include dibasic acid half-ester derivatives of cellulose, which derivatives contain free carboxyl groups, e.g., cellulose acetate hydrogen phthalate, cellulose, acetate hydrogen gluturate, cellulose acetate hydrogen succinate, ethyl cellulose hydrogen succinate, ethyl cellulose acetate hydrogen succinate, cellulose acetate succinate hydrogen phthalate; ether and ester derivatives of cellulose modified with sulfoanhydrides, e.g., with ortho-sulfobenzoic anhydride; polystyrene sulfonic acid; carboxymethyl cellulose; polyvinyl hydrogen phthalate; polyvinyl acetate hydrogen phthalate; polyacrylic acid, acetals of polyvinyl alcohol with carboxy or sulfo-substituted aldehydes, e.g., o-, m- or p-benzaldehyde sulfonic acid or carboxylic acid; partial esters of ethylene/maleic anhydride copolymers; partial esters of methylvinyl ether/maleic anhydride copolymers; etc. In addition, solid monomeric acid materials could also be used such as palmitic acid, oxalic acid, sebacic acid, hydrocinnamic acid, metanilic acid, para-toluenesulfonic acid and benzenedisulfonic acid. Other suitable materials are disclosed in *Research Disclosure*, July, 1974, pp. 17-19.

The pH-lowering layer is usually about 0.3 to about 1.5 mils in thickness and can be located in the receiver portion of the film unit between the support and the image-receiving layer, on the cover sheet, or anywhere within the film unit as long as the desired function is obtained.

An inert timing or spacer layer coated over the pH-lowering layer may also be used to "time" or control the pH reduction of the film unit as a function of the rate at which the alkali diffuses through the inert spacer layer. Timing layers can also be used effectively to isolate development restrainers in a layer adjacent the image-receiving layer wherein restrainers will be released after alkali breakdown of the timing layer. Examples of such timing layers include gelatin, polyvinyl alcohol or any of those disclosed in U.S. Pat. No. 3,455,686 and Research Disclosure, July, 1974, pp. 17-19. The timing layer is also effective in evening out the various reaction rates over a wide range of temperatures, e.g., premature pH reduction is prevented when imbibition is effected at temperatures above room temperature, for example, at 95 to 100° F. The timing layer is usually about 0.1 to about 0.7 mil in thickness. Especially good results are obtained when the timing layer comprises a hydrolyzable polymer or a mixture of such polymers which are slowly hydrolyzed by the processing composition. Examples of such hydrolyzable polymers include polyvinyl acetate, polyamides, cellulose esters, etc.

The alkaline processing composition employed in this invention can be conventional aqueous solutions of an alkaline material, e.g., sodium hydroxide, sodium carbonate or an amine such as diethylamine, preferably possessing a pH in excess of 12, and preferably contains a developing agent as described previously. The solution also preferably contains a viscosity-increasing compound such as a high-molecular-weight polymer, e.g., a water-soluble ether inert to alkaline solutions such as hydroxyethyl cellulose or alkali metal salts of carboxymethyl cellulose such as sodium carboxymethyl cellulose. A concentration of viscosity-increasing compound of about 1 to about 5% by weight of the processing solution is preferred which will impart thereto a viscosity of about 100 cps. to about 200,000 cps.

The alkaline processing composition employed in this invention can also contain a desensitizing agent such as methylene blue, nitro-substituted heterocyclic compounds, 4,4'-bipyridinium salts, etc., to insure that the photosensitive element is not further exposed after it is removed from the camera for processing.

While the alkaline processing composition used in this invention can be employed in a rupturable container, as described previously, to facilitate conveniently the introduction of processing composition into the film unit, other means of discharging processing composition within the film unit could also be employed, e.g., interjecting processing solution with communicating members similar to hypodermic syringes which are attached either to a camera or camera cartridge, as described in Harvey, U.S. Pat. No. 3,352,674 issued Nov. 14, 1967.

In certain embodiments of our invention, and especially with integral format film units, an opacifying agent can be employed in the processing composition in our invention. Examples of opacifying agents include carbon black, barium sulfate, zinc oxide, barium stearate, silver flake, silicates, alumina, zirconium oxide, zirconium acetyl acetate, sodium zirconium sulfate, kaolin, mica, titanium dioxide, organic dyes such as the nigrosines, or mixtures thereof in widely varying amounts depending upon the degree of opacity desired. In general, the concentration of opacifying agent should be sufficient to prevent further exposure of the film unit's silver halide emulsion or emulsions by ambient actinic radiation through the layer of processing composition, either by direct exposure through a support or by light piping from the edge of the element. For example, carbon black or titanium dioxide will generally provide sufficient opacity when they are present in the processing solution in an amount of from about 5 to 40% by weight. After the processing solution and opacifying agent have been distributed into the film unit, processing may take place out of the camera in the presence of actinic radiation in view of the fact that the silver halide emulsion or emulsions of the laminate are appropriately protected by incident radiation, at one major surface by the opaque processing composition and at the remaining major surface by an alkaline solution-permeable opaque layer. Opaque binding tapes can also be used to prevent edge leakage of actinic radiation incident on the silver halide emulsion. In certain embodiments, ballasted indicator dyes or dye precursors can be incorporated in a layer on the exposure side of the photosensitive layers; the indicator dye is preferably transparent during exposure and becomes opaque when contacted with the processing composition.

When titanium dioxide or other white pigments are employed as the opacifying agent in the processing composition in our invention, it may also be desirable to employ in cooperative relationship therewith a pH-sensitive opacifying dye such as a phthalein dye. Such dyes are light-absorbing or colored at the pH at which image formation is effected and colorless or not light-absorbing at a lower pH.

The alkaline solution-permeable, substantially opaque, light-reflective layer in the integral negative receiver film units of our invention can generally comprise any opacifier dispersed in a binder as long as it has the desired properties. Particularly desirable are white light-reflective layers since they would be esthetically pleasing backgrounds on which to view a transferred dye image and would also possess the optical properties desired for reflection of incident radiation. Suitable opacifying agents include titanium dioxide, barium sulfate, zinc oxide, barium stearate, silver flake, silicates, alumina, zirconium oxide, zirconium acetyl acetate, sodium zirconium sulfate, kaolin, mica, or mixtures thereof in widely varying amounts depending upon the degree of opacify desired. The opacifying agents may be dispersed in any binder such as an alkaline solution-permeable polymeric matrix such as, for example, gelatin, polyvinyl alcohol, and the like. Such an opaque layer would generally have a density of at least 4 and preferably greater than 7 and would be substantially opaque to actinic radiation. The opaque layer may also be combined with a developer scavenger layer if one is present. The light-reflective and opaque layers are generally 1 to 6 mils in thickness, although they can be varied depending upon the opacifying agent employed, the degree of opacity desired, etc.

The supports of the film elements of this invention can be any material as long as it does not deleteriously affect the photographic properties of layers thereon and is substantially dimensionally stable. Typical useful supports, include cellulose nitrate film, cellulose acetate film, poly(vinyl acetal) film, polystyrene, film, poly(ethyleneterephthalate) film, polycarbonate film, poly-α- olefins such as polyethylene and polypropylene film, and related films or resinous materials, as well as glass. In those embodiments where the support is transparent, it is usually about 2 to 6 mils in thickness and may contain an ultraviolet absorber if desired.

The support of the integral negative receiver film assemblies and the cover sheet used with these assemblies of this invention can be any of the materials mentioned above for the support. If desired, an ultraviolet-absorbing material and a material for preventing light piping can be employed in the support or cover sheet.

The photosensitive substances used in this invention are preferably silver halide compositions and can comprise silver chloride, silver bromide, silver bromoiodide, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate or thioether ripened emulsions such as those described in U.S. Pat.Nos. 2,222,264 by Nietz et al., 3,320,069 by Illingsworth, and 3,271,157 by McBride. Surface-image emulsions can be used or internal-image emulsions can be used such as those described in U.S. Pat. Nos.2,592,250 by Davey et al, 3,206,313 by Porter et al, and 3,447,927 by Bacon et al. The emulsions may be regular-grain emulsions such as the type described in Klein and Moisar, *J. Phot. Sci.,* Vol. 12, No.5, Sept./Oct., 1964, pp. 242-251. The silver halide emulsions can be spectrally sensitized by means known in the art including techniques of spectrally sensitizing to provide good color balance under various light illumination as described in Schwan et al, U.S. Pat. No.3,672,898 issued June 27, 1972. The silver halide emulsions can be made, if desired, using techniques to achieve high-camera-speed emulsions having ASA speeds of from 400 to above 1000. If desired, mixtures of surface- and internal-image emulsions can be used as described in Luckey et al, U.S. Pat. Nos. 2,996,382.

Negative-type emulsions can be used or directpositive emulsions can be used such as those described in U.S. Pat. No. 2,184,013 by Leermakers, 2,541,472 by Kendall et al, 3,367,778 by Berriman, 3,501,307 by Illingsworth et al issued Mar. 17, 1970, 2,563,785 by Ives, 2,456,953 by Knott et al, 2,861,885 by Land, 3,761,276 by Evans, 3,761,266 by Milton, 3,761,267 by Gilman et al, 3,736,140 by Collier et al and 3,730,723 by Gilman et al, British Patent No. 723,019 by Schouwenaars, and U.S. Pat. No. 4,011,081 issued Mar. 8, 1977.

In still another embodiment, the intramolecular nucleophilic displacement compounds can be coated in a layer in an alkali-permeable binder on a support to provide what is often referred to as a receiver element. The receiver element can be processed by several methods including positioning it in interfacial contact with a photographic silver halide element in the presence of an alkaline solution and a silver halide developer. In those areas where an oxidizing agent such as oxidized developer diffuses to the receiver layer, the nucleophilic displacement compound will be oxidized, and if it contains a dye moiety it will provide a permanent image dye record in the areas corresponding to the imagewise distribution of oxidizing agent. The remainder of the dye can be removed from the element, for example, by washing, after intramolecular nucleophilic displacement. With proper selection of the image dye-providing moieties, a black-and-white image can be obtained. Also, if the nucleophilic compound contains a tanning agent as the photographically useful moiety, it is possible to obtain a tanned image record in areas where silver halide development does not take place, i.e., a positive image record if a negative emulsion is used.

In this application, certain groups are identified with reference to the periodic table. The reference table is located on pp. 400-1of the *Handbook of Chemistry and Physics,* 39th Ed., Chemical Rubber Publishing Co.

The photographic elements, as described above, generally comprise at least one layer containing photographic recording material, such as silver halide, having associated therewith an immobile compound. The term "associated therewith" is a term of art in the photographic industry and generally refers to said immobile compound in alkaline-permeable relationship with said photographic recording material. The respective materials can be coated in the same layers or separate layers and in continuous or discontinuous layers, as long as they are effectively associated and isolated to provide for the desired reactions before a substantial amount of the intermediate reactant products diffuse into adjacent photographic recording layers, etc.

The invention can be further illustrated by the following examples.

EXAMPLE 1: Preparation of Compound I

Step 1 — Preparation of 4-(4-fluorosulfonylphenylazo)-5-(3-fluorosulfonylphenylsulfonamido)-1-naphthol A solution of 1.8 g. (0.01+mol) of 4-fluorosulfonylaniline in 10 ml. ethanol is cooled below 10° C. and diazotized by adding dropwise 1.2 g. (0.01+mol) isoamyl nitrite. After standing for 15 min at >10° C., the diazonium salt is added dropwise to a slurry of 4.74g. (0.01 mol) of 5-(3-fluorosulfonylphenylsulfonamido)-2-N-methylsulfamoyl-1-naphthol in 50 ml. of mixed acids (1 volume propionic +5volumes acetic acid) and 10 ml. of pyridine that has been cooled below 10° C. When the addition is completed, the reaction mixture is stirred at >10° C. for 1 hr., diluted with water and poured into 600 ml. water. The resulting slurry is made acidic with concentrated HCl, collected on a funnel and washed well with water. After drying about 14hr. in vacuo at 40° C., the yield of Step 1is 6.36 g. (96% yield). TLC, using silica gel and ethyl acetate containing 1% acetic acid, shows one magenta spot.

Step 2

A solution of 12.9 g. (0.0195mol) of the product of Step 1 in 120 ml. of N,N-dimethylformamide (DMF) is added in portions to 15 g. (0.2 mol) of neat 1,3-propanediamine with stirring. The reaction mixture becomes warm. Stirring is continued after the addition until the mixture has cooled to room temperature. The run is then filtered by suction on a sintered glass funnel. The DMF filtrate is poured into 700 ml. of rapidly stirred ether and the mixture allowed to settle. The ether is decanted from an insoluble oil. The oil is dissolved in 200 ml. water with warming, acidified with concentrated HCl and allowed to cool, finally being placed in an ice bath. The precipitate is collected on a sintered glass funnel, washed with a small amount of ice-cold dilute HCl and dried. The yield of dye 2HCl (Step 2) is 13 g.

Step 3

A solution of 5.2 g. (0.01 mol) of 7-chloroformyl-1-methyl-2,1-benzisoxazolin-3-one-5-N-methyloctadecylcarboxamide (acid chloride I-A) in tetrahydrofuran (THF) is added to a stirred suspension of 4.2 g. (0.005 mol) of the dye produced in Step 2 above and 2.5 g. (0.2+mol) triethylamine in 50 ml. DMF. After the addition, the THF is removed on a rotary evaporator. The DMF residue is poured into 200 ml. H₂O, made acidic with concentrated HCl and cooled in the ice bath. The precipitate is collected, washed with water and dried. The dried crude product, is purified by dissolving it in dichloromethane, applying the solution to a column of Florisil, and eluting with 89:10:1 mixture of ethyl acetate-acetone-acetic acid, yielding Compound I.

Acid chloride I-A is prepared according to Example 1-A of Belgian Patent No. 810,195 of July 25, 1974, and has the formula:

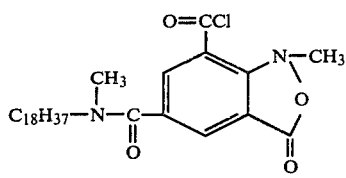

Example 2: Preparation of Compound II

Step 1—Preparation of 5-(3-cyano-4-hydroxyphenylazo)-benzene-1,3-disulfonylfluoride A mixture of 25.7 g. (0.1 mol) 3,5-difluorosulfonylaniline in 100 ml. ethanol and 50 ml. THF is cooled below 10° C. and diazotized by adding 12 g. (0.1+mol) isoamyl nitrite slowly. After the addition, the run is stirred in an ice bath for about 15 min. The solution of diazonium salt is added in portions to a mixture of 11.9 g. (0.1 mol) of o-cyanophenol in 120 ml. mixed acid (1 volume propionic acid and 5 volumes acetic acid) that have been converted to a solution with 25 ml. pyridine and cooled below 10° C. in an ice bath. The coupled mixture is stirred until all of the ice in the bath has melted. Stirring is continued for about 50 hr. at room temperature. Then the run is poured into 1.5 l. water and the insoluble oil is extracted with several portions of ethyl acetate. The combined extracts are washed with three portions of dilute HCl, dried and concentrated. The residue is treated with toluene and concentrated several times to remove acetic and/or propionic acid. The dark oil that remains is dissolved in dichloromethane, applied to a column of Florisil, and eluted with ethyl acetate. The yield of product is 2.8 g.

Step 2: Preparation of 5-[3,5-bis(2-aminoethylsulfamoyl)-phenylazo]-2-hydroxybenzonitrile A solution of the bis(sulfonyl fluoride) of Step 1 in DMF is added to a 10-mol excess of ethylenediamine and worked up according to the procedure of Step 2of Example 1. The oily residue remaining after the ether washings is dissolved in hot aqueous ethanol, made acidic with concentrated HCl and concentrated to dryness. The residue is treated with a small amount of cold dilute HCl and the insoluble material collected and washed with some cold dilute HCl to give the desired product - an azo dye dihydrochloride.

Step 3

The product of Step 2 above is reacted with acid chloride I-A in the manner of Step 3 of Example 1. This is followed by the addition of one equivalent of benzoyl chloride. The reaction mixture is worked up in the same way as Step 3, Example 1. The dried crude product is dissolved in dichloromethane and applied to a column of Florisil. The product is eluted with a mixture of ethyl acetate and 1% acetic acid. The solvent is evaporated and the residue dissolved in ether and precipitated with low-boiling ligroine to afford 1.6 g. of Compound II.

Example 3 Preparation of Compound III

Step 1

A quantity of 13 g. (0.05 mol) 3,5-difluorosulfonylaniline is suspended with rapid stirring in 75 ml. concentrated HCl. After several minutes, 75 ml. water are added and the resulting heavy precipitate is stirred and cooled in an ice bath. The mixture is diazotized by slowly adding a cold solution of 3.6 g. (0.052 mol) sodium nitrite in 10 ml. water and stirring in the cold for about 15 min.

The diazotized aniline is added slowly to a cold slurry of 16.5 g. (0.05 mol) of 5-(4-methanesulfonamido)-2-N-methylsulfamoyl-1-naphthol in 150 ml. mixed acids (1 volume propionic acid, 5volumes acetic acid) to which have been added 70 ml. pyridine. After being stirred in an ice bath for about 1 hr., the coupled mixture is poured with rapid stirring into 200 ml. water and acidified with concentrated HCl to about pH 2. The resulting precipitate is collected, washed well with water and dried in vacuo at about 45° C. The yield of product is 27.5 g. (92%).

Step 2

A solution of 29.9 g. (0.05 mol) of the product of Step 1 above in 300 ml. DMF is added in portions with stirring to 30 g. (0.5 mol) neat ethylenediamine. The reaction mixture becomes warm. After stirring about 30 min., it is poured into 1200 ml. water and acidified to pH 2 with concentrated HCl. After cooling to about ambient temperature, the mixture is cooled further in an ice bath. The precipitate is collected and washed with about 100 ml. cold dilute HCl. After drying in vacuo at aoubt 45° C., 34.7 g. (92% yield) of the desired compound of Step 2 is obtained.

Step 3

A quantity 7.5 g. (0.01 mol) of the product of Step 2 above is reacted with two equivalents of acid chloride I-A according to the procedure of Step 3, Example 1. After removing the THF under reduced pressure, the remainder is poured into 600 ml. dilute HCl. The resulting granular precipitate is collected, washed well with about 200 ml. water and dried. The crude product is dissolved in dichloromethane and applied to a column of Florisil, eluting with a mixture of ethyl acetate:acetone: acetic acid=89:10:1. The eluate is concentrated, dissolved in a minimum of dichloromethane and precipitated with ether. The yield of product is 5 g.

Example 4: Photographic Evaluation

A single-color, integral transfer photographic element is prepared by coating a transparent polyethylene terephthalate film support with the following layers in order from the support:

(1) layer containing the mordant poly(styrene-co-N,N,N-tri-n-hexyl-N-vinylbenzylammonium chloride) at 200 mg./ft.$^2$ and gelatin at 200 mg./ft.$^2$;
(2) layer containing titanium dioxide at 2000 mg./ft.$^2$ and gelatin at 360 mg./ft.$^2$;
(3) layer containing carbon at 250 mg./ft.$^2$ and gelatin at 156 mg./ft.$^2$;
(4) layer containing a negative-working silver bromide emulsion (0.8 micron) at 100 mg. Ag/ft.$^2$, gelatin at 200 mg./ft.$^2$, and Compound I at 104 mg./ft.$^2$ dissolved in diethyl lauramide at 104 mg./ft.$^2$;
(5) layer containing gelatin at 50 mg./ft.$^2$.

The photographic element is exposed to a graduted-density test object and processed at room temperature by rupturing a pod containing a viscous solution comprising 100 g. potassium hydroxide, 20 g. potassium bromide, 3 g. 4-hydroxymethyl-4-methyl-1-phenyl-3-pyrazolidone and 40 g. hydroxyethyl cellulose/liter of water between the photographic element and a cover sheet comprising a polyethylene therephthalate film support having coated thereon in order from the support:

(1) layer containing polyacrylic acid at 1440 mg./ft.$^2$;
(2) layer containing cellulose acetate at 760 mg./ft.$^2$ and copoly(styrene/maleic anhydride) at 38 mg./ft.$^2$.

After a few minutes, a well-defined positive magenta image is viewed through the transparent support of the photographic element.

After keeping samples of the processed element at room temperature and at 140° F. (60° C.), the dye densitites to green light are:
(a) 3 hr. at room temperature: Dmax=1.96; Dmin=0.24
(b) 16 hr. at 140° F. (60° C.): Dmax=1.86; Dmin=0.30

Example 5

A photographic element is prepared, exposed and processed as in Example 4, except that layer 4 contains compound 3 at 58 mg./ft.$^2$ dissolved in diethyl auramide at 58 mg./ft.$^2$ in place of Compound I.

After keeping samples of the processed element at room temperature and at 140° F. (60° C.), the dye densitites to green light are:
(a) 3 hr. at room temperature: Dmax=1.45; Dmin=0.21
(b) 16 hr. t 140° F. (60° C.): Dmax=1.42; Dmin=0.22

Example 6

Part A

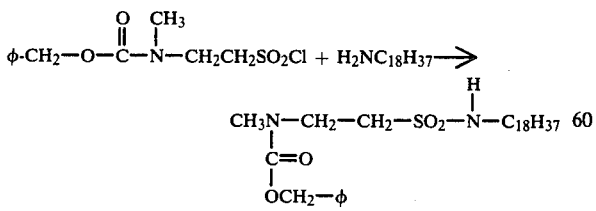

A solution comprising 116.6 g. (0.4 mole) of the above sulfonyl chloride (prepared according to Example 16A, U.S. Ser. No. 534,966) in 500 ml. tetrahydrofuran is cooled in an ice bath with the addition at a fast dropping rate of a solution of 108 g. (0.4 mole) of octadecylamine and 41 g. (0.4 mole) of triethylamine in 600 ml. tetrahydrofuran (THF).

After the addition, the reaction is made acidic with dry HCl gas. After cooling in ice, the precipitated amine hydrochlorides are removed by suction filtration and washed with THF. The filtrate is concentrated on a rotary evaporator. The remaining solid residue is recrystalized from 600 ml. ethanol. Yield 126.4 g. (60%), m.p. 73°–74° C.

Part B—Hydrogenation

To a solution of 126.4 g. (0.24 mole) of the blocked amine in 800 ml. THF are added 200 ml. ethanol. To this solution are added 4 g. 10% palladium on carbon and the mixture is hydrogenated on a Parr shaker (initial pressure, 55 p.s.i.). After 8 hr., the theoretical amount of hydrogen has been absorbed (0.24 mole). The mixture is heated to boiling and filtered hot by suction through a celite pad. The filtrate is concentrated under reduced pressure and the remaining dried solid is used directly.

Part C

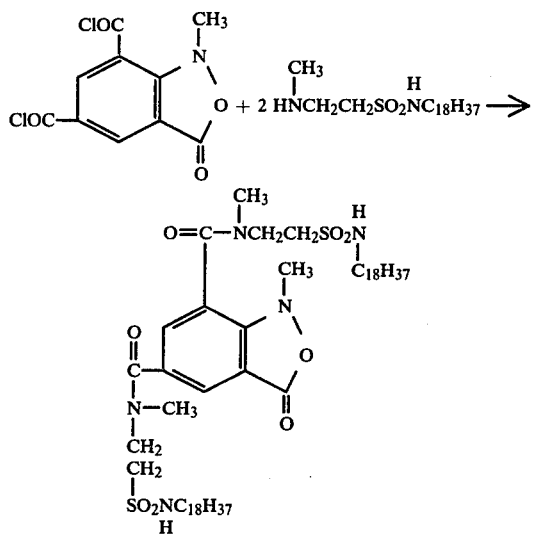

To a stirred solution of 0.1 mole of the bisacid chloride, prepared according to Example 1A, Belgian Pat. No. 810,195 granted July 25, 1974, in 100 ml. of THF cooled in an ice bath is added dropwise a solution of 80 g. (0.204 mole) of the above ballast amine and 25 g. (0.25 mole) of triethylamine in 800 ml. of warm THF. After the addition, the reaction is made acidic with hydrogen chloride gas, cooled in ice and the precipitated amine hydrochlorides removed by suction filtration. The filtrate is concentrated to dryness under reduced pressure and the residue recrystallized from 600 ml. of ethanol, giving 84.1 g. (86%) of the bis-amide product.

Part D

To a solution of 84 g. (0.0855 mole) of the bisamide of Part C in 300 ml. of THF are added 500 ml. of ethanol. The stirred solution is purged with nitrogen for about 30 min. Then a solution of 14 g. (0.34 mole) of sodium hydroxide in 100 ml. of water is added all at once. The reaction is stirred under nitrogen at room temperature for 15 min., then made acidic with concentrated hydrochloric acid. The mixture is diluted with 2800 ml. of water, the solid collected, washed with water and dried.

The dry solid is stirred with 800 ml. of THF and filtered. The filtrate is concentrated under reduced pressure and the residue recrystallized from 300 ml. of methanol containing 4 ml. of 6N hydrochloric acid. Yield 31.2 g. of the ballasted acid, m.p. 129°–131° C.

Part E

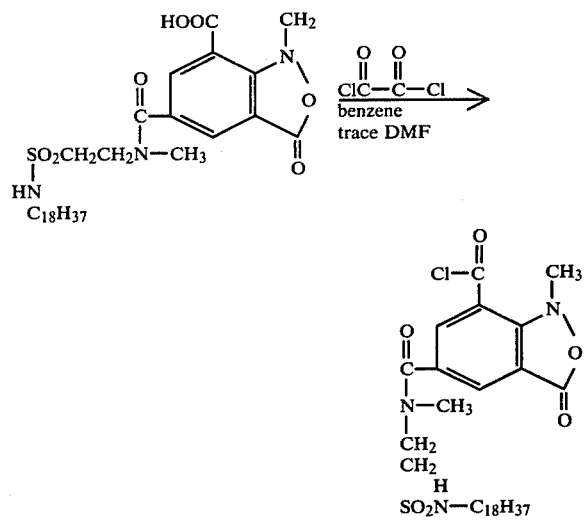

To a well-stirred slurry of 6.09 g. (0.01 mole) of the acid in 60 ml. of benzene are added 1.5 g. of oxalyl chloride, followed by 2 drops of dimethylformamide. The reaction is stirred and warmed to about 50° C. until a clear solution is obtained (about 45 min. to 1 hr.). The yellow solution is then concentrated to dryness of a rotary evaporator. The remaining yellow foam is used directly.

Part F

The bis-amine release dye from Example 3, Step 2, is reacted with two equivalents of the acid chloride of Part E according to the procedures of Step 3, Example 1, to produce Compound IV.

Example 7

Compounds V-XVII have been prepared by the general method specified in Examples 1-3 where the appropriate starting materials are used to obtain the respective compounds.

Example 8

Compounds IV-XVII have been evaluated in image-transfer film units by the same procedure as set forth in Examples 4–5. In each instance, a well-defined positive image is observed in the mordant layer.

Multicolor image-transfer elements can be prepared using the yellow, cyan and magenta compounds in the respective blue, red and green layers of a photographic image-transfer element with the respective dyes of the compounds providing a color image corresponding to the exposure test pattern upon processing for 3–6 minutes.

Although the invention has been described in considerable detail with particular reference to certain preferred embodiments thereof, variations and modifications can be effected within the spirit and scope of the invention.

We claim:

1. A photographic element comprising a support having thereon at least one alkali-permeable layer containing an immobile compound comprising a photographically useful moiety which is an image dye-providing material or a photographic reagent, said compound containing a) at least two oxidizable nucleophilic groups or precursors for oxidizable nucleophilic groups and b) at least two electrophilic cleavage groups, each of which contains an electrophilic group and a leaving group which can be displaced by one of said nucleophilic groups under alkaline conditions, linking said photographically useful moiety to separate groups which are each a ballast rendering said compound immobile under alkaline processing conditions in said element and each ballast being capable of substantially immobilizing said photographically useful moiety after the cleavage of said other ballast groups, said nucleophillic groups being located in said compound relative to each said electrophilic cleavage group to provide for intramolecular nucleophilic displacement of said leaving group from said electrophilic group cleaving said photographically useful moiety from said ballast groups under said alkaline conditions, said nucleophilic group and said electrophilic group are each attached to an aromatic ring and contain from 1–5 atoms between the nucleophilic center of said nucleophilic group and the electrophilic center of said electrophilic group, whereby said compound is capable of forming a ring having from 3–7 atoms therein by intramolecular nucleophilic displacement, and said compound upon oxidation of one of said nucleophilic groups having a substantially lower rate of release of said photographically useful moiety under said alkaline conditions, and wherein the rate of reaction of said compound with an oxidized silver halide developing agent is substantially faster than the reaction rate of intramolecular nucleophilic displacement under alkaline processing conditions.

2. A photographic element according to claim 1 wherein said compound contains a hydrolyzable precursor for each of said nucleophilic groups.

3. A photographic element according to claim 1 wherein said compound contains a hydrolyzable precursor for each of said nucleophilic groups which is present in a benzisoxazolone moiety in said compound.

4. A photographic element according to claim 1 wherein the rate of reaction of said compound with an oxidized 3-pyrazolidone silver halide developing agent is substantially faster than the reaction rate of intramolecular nucleophilic displacement under alkaline processing conditions.

5. A photographic element according to claim 4 wherein the rate of oxidation of said compound is at least ten times faster than the rate of nucleophilic displacement.

6. A photographic element according to claim 1 wherein said photographically useful moiety is an image dye or image-dye precursor.

7. A photographic element according to claim 6 comprising at least one layer containing a silver halide emulsion which has associated therewith said immobile compound.

8. A photographic element according to claim 1 wherein release of said photographically useful moiety is substantially prevented upon oxidation of one of said nucleophilic groups of said immobile compound.

9. A photographic element comprising a support having thereon at least three separate superposed layers each containing a silver halide emulsion and each having associated therewith an immobile compound containing a photographically useful group which is an image dye or image- dye precursor, each said compound containing (a) at least two oxidizable nucleophilic groups or precursors for oxidizable nucleophilic groups and (b) at least two electrophilic cleavage groups, each of which contains an electrophilic group and a leaving group which can be displaced by one of said nucleophilic groups under alkaline conditions, linking said photographically useful moiety to separate groups which are each a ballast rendering said compound immobile under alkaline processing conditions in said element and each ballast being capable of substantially immobilizing said photographically useful moiety after the cleavage of said other ballast groups, said nucleophilic groups being located in said compound relative to each said electrophilic cleavage group to provide for intramolecular nucleophilic displacement of said leaving group from said electrophilic group cleaving said photographically useful moiety from said ballast groups under said alkaline conditions, said nucleophilic group and said electrophilic group are each attached to an aromatic ring and contain from 1-5 atoms between the nucleophilic center of said nucleophilic group and the electrophilic center of said electrophilic group, whereby said compound is capable of forming a ring having from 3-7 atoms therein by intramolecular nucleophilic displacement, and said compound upon oxidation of one of said nucleophilic groups having a substantially lower rate of release of said photographically useful moiety under said alkaline conditions, and wherein said immobile compounds have a rate of release of said photographically useful group which is less than the rate of reaction with oxidized silver halide developer but is faster than the rate of substantial fog development in the initially undeveloped areas of said silver halide emulsions.

10. A photographic element according to claim 9 wherein said silver halide developer is a 3-pyrazolidone compound, a catechol compound or a hydroquinone compound.

11. A photographic element according to claim 9 wherein said immobile compounds contain said image dye which is diffusible upon cleavage from said ballast groups.

12. A photographic element according to claim 9 which further contains a development restrainer which permits initial development to take place but substantially represses further development.

13. A photographic element according to claim 1 wherein said immobile compound contains said precursor for a nucleophilic group which is a precursor for an hydroxyamino group and said photographically useful moiety is a preformed diffusible dye.

14. A photographic element according to claim 1 wherein said immobile compound contains a benzisoxazolone group which provides a precursor for one of said nucleophilic groups.

15. A photographic element comprising a support and at least one layer thereon containing an alkalipermeable layer and an immobile compound having the formula:

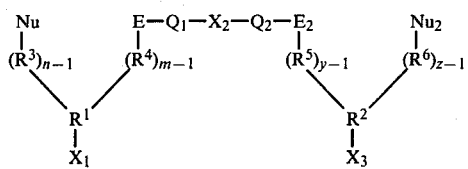

wherein $R^1$ and $R^2$ are each an acyclic or cyclic organic group; $R^3$, $R^4$, $R^5$ and $R^6$ are each bivalent organic groups containing from 1-3 atoms in the bivalent linkage; n, m, y and z are each integers of 1 or 2; Nu and $Nu_2$ are each oxidizable nucleophilic groups or precursors therefor; E and $E_2$ are each an electrophilic group; $Q_1$ and $Q_2$ are each a bivalent group providing a mono atom linkage between E and $X_2$ and $E_2$ and $X_2$ wherein said mono atom is a nonmetallic atom of group VA or VIA of the periodic table in its minus 2 or minus 3 valence state which can be displaced from said electrophilic group by said nucleophilic group under alkaline conditions; $Q_1$-$X_2$-$Q_2$ is an image dye-providing moiety or a photographic reagent; $X_1$ and $X_3$ are each a ballasting group of a size sufficient to render $Q_1$-$X_2$-$Q_2$ immobile in an alkaline processing medium in an alkali-permeable layer of the photographic element; and said nucleophilic groups being located in said compound relative to said electrophilic groups to provide for intramolecular nucleophilic cleavage of $Q_1$-$X_2$-$Q_2$ from the remainder of the compound under alkaline conditions, and said compound upon oxidation of at least one of said nucleophilic groups having a substantially lower rate of release of said image dye-providing moiety or photographic reagent in an alkaline medium, and wherein the rate of reaction of said compound with an oxidized silver halide developing agent is substantially faster than the reaction rate of intramolecular nucleophilic displacement under alkaline processing conditions.

16. A photographic element according to claim 15 wherein $R^1$ and $R^2$ of said compound are each an aromatic ring and n, m, y and z are each 1.

17. A photographic element according to claim 15 wherein $Q_1$-$X_2$-$Q_2$ of said compound is an image dye or image-dye precursor.

18. A photographic element according to claim 15 wherein Nu and $Nu_2$ are each a hydrolyzable precursor for said nucleophilic groups.

19. A photographic element according to claim 15 wherein n, m, y and z are 1, and $R^1$ and $R^2$ are each an aromatic ring having electron-withdrawing groups substituted thereon.

20. A photographic element according to claim 19 wherein at least one of $X_1$ and $X_3$ contains a base ionizable group.

21. A photographic element according to claim 15 wherein said immobile compound has the formula:

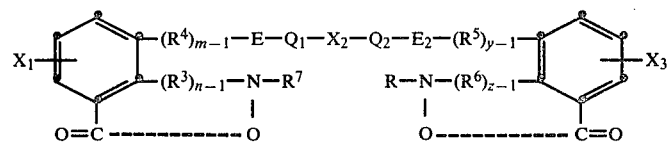

wherein R³, R⁴, R⁵ and R⁶ are each bivalent organic groups containing from 1-2 atoms; R⁷ is an alkyl group or an aryl group; E and E₂ are each an electrophilic group; Q₁ and Q₂ are each a bivalent group providing a mono atom linkage between E and X₂ and E₂ and X₂ wherein said mono atom is a nonmetallic atom of group VA or VIA of the periodic table in its −2 or −3 valence state which can be displaced from said electrophilic group by said nucleophilic group under alkaline conditions; Q₁-X₂-Q₂ is an image dye-providing moiety or a photographic reagent; X₁ and X₃ are each a group of a size sufficient to render Q₁-X₂-Q₂ immobile under alkaline processing conditions in an alkali-permeable layer of the photographic element; and n, m, y and z are integers of 1 or 2, and wherein the rate of reaction of said compound with an oxidized silver halide developing agent is substantially faster than the reaction rate of intramolecular nucleophilic displacement under alkaline processing conditions.

22. A photographic element according to claim 15 wherein said photographic element comprises at least one layer containing a silver halide emulsion which has associated therewith said immobile compound.

23. A photographic element comprising a support having thereon at least one layer comprising a silver halide emulsion having associated therewith an immobile compound, wherein said immobile compound has the formula:

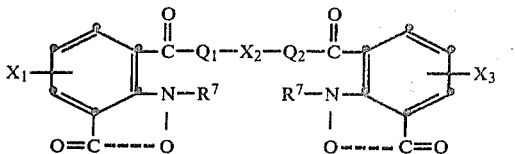

wherein each R⁷ is an alkyl group or an aryl group; Q₁ and Q₂ are each a bivalent group providing a mono atom linkage between the carbonyl group and X₂ wherein said mono atom is a nonmetallic atom of group VA or VIA of the periodic table in its −2 or −3 valence state which can be displaced from the adjacent carbonyl group by a hydroxylamino nucleophilic group under alkaline conditions; X₁ and X₃ are each a group of a size sufficient to render Q₁-X₂-Q₂ immobile under alkaline processing conditions in an alkali-permeable layer of the photographic element; and Q₁-X₂-Q₂ is an image dye-providing moiety or a photographic reagent.

24. A photographic element according to claim 23 wherein Q₁ and Q₂ are each an amino group.

25. A photographic element according to claim 23 wherein Q₁-X₂-Q₂ is a development restrainer.

26. A photographic element according to claim 23 wherein Q₁-X₂Q₂ is a dye or dye precursor.

27. A photographic element according to claim 23 wherein X₁ and X₃ are each a ballast group having at least 8 carbon atoms therein, Q₁-X₂-Q₂ is an image dye or dye precursor, Q₁ and Q₂ are each an amino group, and R⁷ is an alkyl group.

28. A photographic element according to claim 23 wherein said immobile compound has the formula:

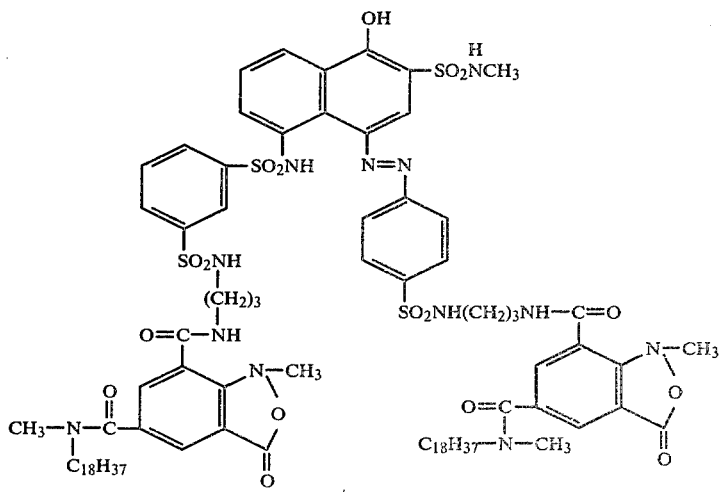

29. A photographic element according to claim 23 wherein said immobile compound has the formula:

30. A photographic element according to claim 23 wherein said immobile compound has the formula:

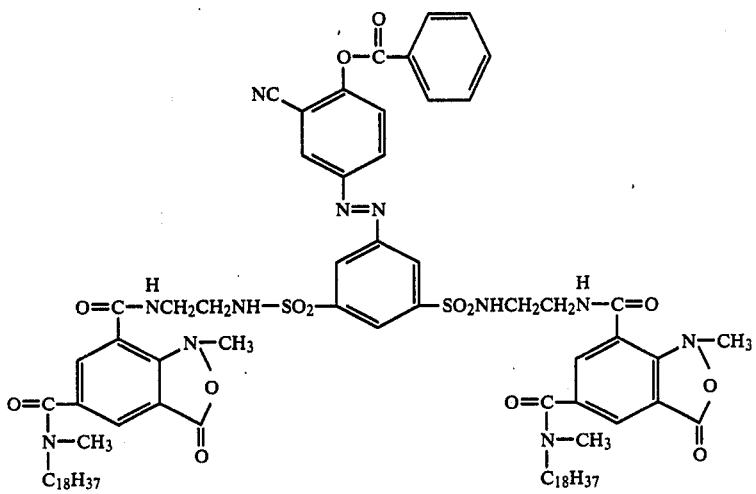

31. A photographic element according to claim 23 wherein $Q_1$-$X_2$-$Q_2$ is a dye moiety having solubilizing groups thereon and is diffusible through colloid layers of a photographic element in an alkaline medium.

32. In a film unit adapted to be processed by passing said unit between a pair of juxtaposed pressure-applying members comprising:
  (a) a photographic element comprising a support having thereon at least one layer containing a silver halide emulsion having associated therewith an image dye providing material;
  (b) an image dye-receiving layer;
  (c) means containing an alkaline processing solution which is adapted to discharge said solution within said film unit; and
  (d) a silver halide developing agent which is soluble in said alkaline processing solution;
the improvement wherein said film unit comprises an immobile compound which provides said image dye-providing material or which contains a photographic reagent and said immobile compound contains (i) at least two oxidizable nucleophilic groups or hydrolyzable precursors for nucleophilic groups and (ii) at least two electrophilic cleavage groups, each of which contains an electrophilic group and a leaving group which can be displaced by one of said nucleophilic groups under alkaline conditions, linking a photographically useful moiety, which is an image dye-providing moiety or a photographic reagent, to separate groups, each of

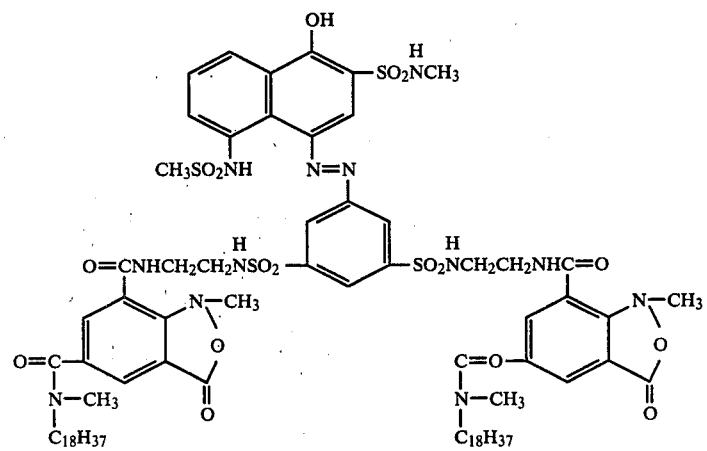

which is a ballast rendering said compound immobile under alkaline processing conditions in said element and each ballast being capable of substantially immobilizing said photographically useful moiety after the cleavage of said other ballast groups, said nucleophilic groups being located in said compound relative to each said electrophilic cleavage group to provide for intramolecular nucleophilic displacement of said leaving group from said electrophilic group cleaving said photographically useful moiety from said ballast groups under said alkaline conditions, said nucleophilic group and said electrophilic group are each attached to an aromatic ring and contain from 1–5 atoms between the nucleophilic center of said nucleophilic group and the electrophilic center of said electrophilic group, whereby said compound is capable of forming a ring having from 3–7 atoms therein by intramolecular nucleophilic displacement, and said compound upon oxidation of one of said nucleophilic groups having a substantially lower rate of release of said photographically useful moiety under said alkaline conditions wherein the rate of reaction of said compound with an oxidized silver halide developing agent is substantially faster than the reaction rate of intramolecular nucleophilic displacement under alkaline processing conditions.

33. A film unit according to claim 32 wherein said photographic element comprises at least three said layers, each containing a silver halide emulsion having associated therewith an immobile compound which contains a photographically useful moiety and wherein said photographically useful moiety is an image dye or image-dye precursor.

34. A film unit according to claim 32 wherein said silver halide developing agent is a 3-pyrazolidone compound, a hydroquinone compound or a catechol compound.

35. A film unit according to claim 32 wherein said immobile compound comprises a hydrolyzable precursor for said nucleophilic group and said photographically useful moiety is an image dye or imge-dye precursor.

36. A film unit according to claim 32 wherein said immobile compound contains a 2,1-benzisoxazolone group which provides one of said precursors for a nucleophilic group.

37. a film unit according to claim 32 wherein said photographically useful moiety is a development restrainer.

38. A film unit according to claim 32 wherein said photographically useful moiety is a development restrainer comprising a phenylmercaptotetrazole.

39. A film unit according to claim 32 wherein said photographically useful moiety is a photographic reagent.

40. A photographic film unit according to claim 32 wherein said immobile compound comprises said hydrolyzable precursor for a nucleophilic group, said electrophilic group is a carbonyl group and said photographically useful moiety is an image dye-providing group.

41. In a film unit comprising:
(a) a photographic element comprising a transparent support having thereon, in sequence, (i) a dye image-receiving layer, (ii) an opaque alkali-permeable layer and (iii) at least one layer containing a silver halide emulsion having associated therewith an image dye-providing material;
(b) means containing an alkaline processing composition adapted to discharge said composition within said film unit;
(c) a silver halide developing agent which is soluble in said alkaline processing composition; and
(d) a cover sheet which can be superposed or adapted to be superposed on said photographic element;
the improvement wherein said image dye-providing material is an immobile compound containing:
(a) two separate electrophilic cleavage groups, each of which contains an electrophilic group and a leaving group;
(b) a diffusible image dye-providing moiety;
(c) two ballast groups for immobilizing said compound in an alkali-permeable colloid layer at least under alkaline conditions wherein each ballast group is of sufficient size to render said compound substantially immobile after cleavage of the other said ballast group;
(d) two separate oxidizable nucleophilic groups or precursors for said oxidizable nucleophilic groups which have a rate of reaction with oxidized silver halide developing agent which is substantially faster than the rate of reaction with said electrophilic cleavage groups and which:
(i) are each located in said compound where in the unoxidized form they react with one of said electrophilic cleavage groups under alkaline conditions to displace said leaving group from said electrophilic group cleaving said ballast group from said image dye-providing moiety, and
(ii) in the oxidized form do not react with said electrophilic group under alkaline conditions;
(e) said image dye-providing moiety being linked to each said ballast group through one of said electrophilic cleavage groups; and said immobile compound has the formula;

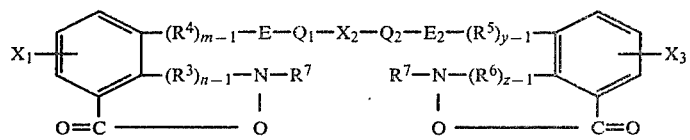

wherein $R^3$, $R^4$, $R_5$ and $R^6$ are each bivalent organic groups containing from 1-2 atoms; each $R^7$ is an alkyl group or an aryl group; E and $E_2$ are each an electrophilic group; $Q_1$ and $Q_2$ are each a bivalent group providing a mono atom linkage between E and $X_2$ wherein said mono atom is a nonmetallic atom of group VA or VIA of the periodic table in its -2 or -3 valence state; $Q_1$-$X_2$-$Q_2$ is an image dye-providing moiety or a photographic reagent; $X_1$ and $X_3$ are each a group of a size sufficient to render $Q_1$-$X_2$-$Q_2$ immobile under alkaline processing conditions in an alkali-permeable layer of the photographic element; and n, m, y and z are integers of 1 or 2.

42. A film unit according to claim 41 wherein said photographic element comprises at least three separate layers, each of which contains a silver halide emulsion having associated therewith an immobile compound which contains an image dye or dye precursor.

43. A film unit according to claim 41 wherein said cover sheet is a transparent film support which is superposed on said photographic element and said alkaline processing solution comprises an opacifying material.

44. A photographic element comprising a support having thereon at least one alkali-permeable layer containing a silver halide emulsion having associated therewith an immobile compound comprising a photographically useful moiety which is an image dye-providing material or a photographic reagent, said compound containing a) at least two oxidizable nucleophilic groups or precursors for oxidizable nucleophilic groups and b) at least two electrophilic cleavage groups, each of which contains an electrophilic group and a leaving group which can be displaced by one of said nucleophilic groups under alkaline conditions, linking said photographically useful moiety to separate groups which are each a ballast rendering said compound immobile under alkaline processing conditions in said element and each ballast being capable of substantially immobilizing said photographically useful moiety after the cleavage of said other ballast group, said nucleophilic groups being located in said compound relative to each said electrophilic cleavage group to provide for intramolecular nucleophilic displacement of said leaving group from said electrophilic group cleaving said photographically useful group from said ballast groups under alkaline conditions, said nucleophilic group and said electrophilic group are each attached to an aromatic ring and contain from 1–5 atoms between the nucleophilic center of said nucleophilic group and the electrophilic center of said electrophilic group, whereby said compound is capable of forming a ring having from 3–7 atoms therein by intramolecular nucleophilic displacement, and said compound upon oxidation of one of said nucleophilic groups having a substantially lower rate of release of said photographically useful group in an alkaline medium and wherein the rate of reaction of said compound with an oxidized silver halide developing agent is substantially faster than the reaction rate of intramolecular nucleophilic displacement under alkaline processing conditions.

45. A photographic element according to claim 44 containing a silver halide developer having associated therewith said immobile compound.

46. A photographic element according to claim 44 containing at least three separate layers, each of which contains silver halide emulsion and each of which has one of said immobile compounds associated therewith.

47. A photographic element according to claim 44 containing three separate layers, each of which contains a silver halide emulsion and each of which has associated therewith a different immobile compound according to the formula:

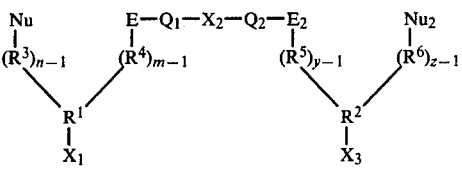

wherein $R^1$ and $R^2$ are each an acyclic or cyclic organic group; $R^3$, $R^4$, $R^5$ and $R^6$ are each bivalent organic groups containing from 1–3 atoms in the bivalent linkage; n, m, y and z are each integers of 1 or 2; Nu and $Nu_2$ are each oxidizable nucleophilic groups or precursors therefor; E and $E_2$ are each an electrophilic group; $Q_1$ and $Q_2$ are each a bivalent group providing a mono atom linkge between E and $X_2$ and $E_2$ and $X_2$ wherein said mono atom is a nonmetallic atom of group VA or VIA of the periodic table in its minus 2 or minus 3 valence state; $Q_1$-$X_2$-$Q_2$ is an image dye-providing moiety or a photographic reagent; $X_1$ and $X_3$ are each a ballasting group of a size sufficient to render $Q_1$-$X_2$-$Q_2$ immobile in an alkaline processing medium in an alkalipermeable layer of the photographic element; and said nucleophilic groups being located in said compound relative to said electrophilic groups to provide for intramolecular nucleophilic cleavage of $Q_1$-$X_2$-$Q_2$ from the remainder of the compound under alkaline conditions, and said compound upon oxidation of at least one of said nucleophilic groups having a substantially lower rate of release of said photographically useful group in an alkaline medium.

* * * * *